United States Patent [19]
Kosley, Jr. et al.

[11] Patent Number: 5,374,650
[45] Date of Patent: Dec. 20, 1994

[54] CARBAMOYLOXYLABDANES

[75] Inventors: Raymond W. Kosley, Jr., Bridgewater; Robert J. Cherill, Somerset, both of N.J.; Gerard O'Malley, Newton, Pa.

[73] Assignee: Hoechst-Roussel Pharmaceuticals, Inc., Somerville, N.J.

[21] Appl. No.: 37,148

[22] Filed: Mar. 25, 1993

Related U.S. Application Data

[60] Continuation of Ser. No. 443,526, Nov. 29, 1989, abandoned, which is a division of Ser. No. 137,998, Dec. 28, 1987, Pat. No. 4,920,146, which is a continuation-in-part of Ser. No. 947,070, Dec. 29, 1986, abandoned.

[51] Int. Cl.$^5$ .................. A61K 31/41; A61K 31/36; C07D 239/20; C07D 319/08
[52] U.S. Cl. .......................... 514/397; 514/228.2; 514/232.8; 514/253; 514/232.5; 514/365; 514/374; 514/434; 514/435; 514/452; 514/453; 514/228.5; 544/60; 544/150; 544/378; 546/197; 548/146; 548/215; 548/341.5; 548/526; 549/15; 549/18; 549/358; 549/387
[58] Field of Search .......................... 544/60, 150, 378; 546/197; 548/146, 215, 341.5, 526; 549/358, 389, 15, 18; 514/227, 232.8, 253, 231, 365, 374, 397, 434, 435, 452, 453

[56] References Cited

U.S. PATENT DOCUMENTS

| | | | |
|---|---|---|---|
| 3,631,039 | 12/1971 | Andrews | 260/247.7 A |
| 4,088,659 | 5/1978 | Bhat et al. | 260/345.2 |
| 4,118,508 | 10/1978 | Bhat et al. | 424/283 |
| 4,134,986 | 1/1979 | Bajwa et al. | 424/283 |
| 4,476,140 | 10/1984 | Sears | 424/283 |
| 4,517,200 | 5/1985 | Kreutner et al. | 514/455 |
| 4,564,626 | 1/1986 | Kreutner et al. | 514/430 |
| 4,639,443 | 1/1987 | Kosley et al. | 514/222 |
| 4,639,446 | 1/1987 | Kosley | 514/222 |
| 4,920,146 | 4/1990 | Kosley, Jr. et al. | 514/437 |
| 5,093,336 | 3/1992 | Kosley, Jr. et al. | 514/269 |

FOREIGN PATENT DOCUMENTS

| | | |
|---|---|---|
| 0126313 | 11/1984 | European Pat. Off. |
| 0189801 | 8/1986 | European Pat. Off. |
| 0191166 | 8/1986 | European Pat. Off. |
| 0192056 | 8/1986 | European Pat. Off. |
| 0193132 | 9/1986 | European Pat. Off. |
| 0217372 | 4/1987 | European Pat. Off. |
| 2654796 | 6/1978 | Germany |
| 3346869 | 7/1984 | Germany |
| 3407514 | 9/1985 | Germany |
| 3502686 | 8/1986 | Germany |
| 3623300 | 1/1988 | Germany |

OTHER PUBLICATIONS

A. Laurenza, et al., Molecular Pharmacology, 32, 133 (1987).

CALBIOCHEM Biochemical/Immunochemical Catalog, 1988 New Product supplement, p. 18.

S. P. Bartels, et al., Current Eye Research, 2, 673 (Feb. 1983).

R. J. Cherill, et al., Abstracts of Papers, 192nd ACS National Meeting, Medi, No. 48 (Sep. 1986).

J. Caprioli and M. Sears, The Yale Journal of Biology and Medicine, 57, 283 (1984).

K. B. Seamon and J. W., Daly, Trends in Pharmacological Sciences, 48,120 (1983).

K. B. Seamon and J. W. Daly, J., Cyclic Nucleotide Research, 7, 201 (1981).

J. Caprioli, et al., Abstracts, Association for Research in Vision and Ophthalmology, 233 (1986).

S. P. Bartels, et al., Current Eye Research, 6, 307 (1987).

K. B. Seamon and J. W. Daly, in "Advances in Cyclic Nucleotide and Protein Phosphorylation Research", vol. 20, P. Greengard and G. A. Robison, Editors, Raven Press, New York, N.Y., 1986, pp. 1 to 150.

N. J. de Sousa, et al., Medicinal Research Reviews, 3, 201 (1983).

S. V. Bhat, et al., J. Med. Chem.,26,486 (1983).

K. B. Seamon, et al., J. Med. Chem.,26, 436 (1983).

S. V. Bhat, et al., Tetrahedron Letters, 1669 (1977).

S. V. Bhat, et al., J. C. S. Perkin I, 767 (1982).

J. Caprioli, et al., Investigative Ophthalmology and Visual Science, 25, 268 (1984).

J. Caprioli and M. Sears, The Lancet, 958 (1983).

K. B. Seamon, et al., Proc. Natl. Acad. Sci, USA 78, 3363 (1981).

K. Seamon and J. W. Daly, The Journal of Biological Chemistry, 256, 9799(1981).

J. Takeda, et al., The Journal of Investigative Dermatology, 81, 236 (1983).

J. Takeda, et al., The Journal of Investigative Dermatology, 81, 131 (1983).

H. Hzuka, et al., Biochimica et Biophysica Acta., 444, 685 (1976).

H. Hzuka, et al., Biochimica et Biophysica Acta., 437, 150 (1976).

J. J. Voorhees, The Journal of Investigative Dermatology, 59, 114 (1972).

K. M. Halprin, et al., The Journal of Investigative Dermatology, 65, 170 (1975).

W. P. Raab, International Journal of Clinical Pharmacology, Therapy and Toxicology, 18, 212 (1980).

*Primary Examiner*—C. Warren Ivy
*Assistant Examiner*—Ba K. Trinh
*Attorney, Agent, or Firm*—Raymond R. Wittekind

[57] ABSTRACT

Novel carbamoyloxylabdanes, intermediates and processes for the preparation thereof, and methods for reducing intraocular pressure and treating cardiac failure utilizing compounds and compositions thereof are disclosed.

44 Claims, No Drawings

CARBAMOYLOXYLABDANES

This is a continuation of application Ser. No. 07/443,526 filed Nov. 29, 1989 now abandoned which is a division of application Ser. No. 07/137,998 filed Dec. 28, 1987, now U.S. Pat. No. 4,920,146, which is a continuation-in-part of application Ser. No. 06/947,070 filed Dec. 29, 1986 now abandoned.

The present invention relates to carbamoyloxylabdanes. More particularly, the present invention relates to carbamoyloxylabdanes of the formula 1

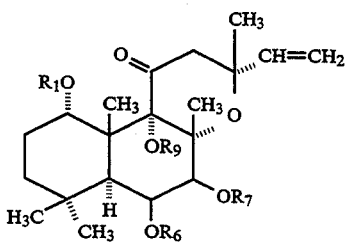

1 wherein:

(a) $R_1$ is hydrogen or a group of the formula

wherein $R_2$ and $R_3$ are independently hydrogen or loweralkyl of 1 to 6 carbon atoms and r is 0 or 1; and $R_2$ and $R_3$ taken together with the nitrogen atom to which they are attached form a group of the formula

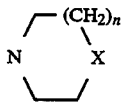

wherein X is O, S, a group of the formula $NR_{19}$ wherein $R_{19}$ is loweralkyl of 1 to 6 carbon atoms or a group of the formula $CHR_4$ wherein $R_4$ is hydrogen, loweralkyl of 1 to 6 carbon atoms or a group of the formula $OR_5$ wherein $R_5$ is hydrogen, loweralkyl of 1 to 6 carbon atoms or a group of the formula

wherein $R_{10}$ is loweralkyl of 1 to 6 carbon atoms and n is 0 or 1;

(b) $R_9$ is hydrogen;

(c) $R_1$ and $R_9$ taken together form a group of the formula CO, a group of the formula SO or a group of the formula $CHNR_{11}R_{12}$ wherein $R_{11}$ and $R_{12}$ are each independently loweralkyl of 1 to 6 carbon atoms; and $R_{11}$ and $R_{12}$ taken together with the nitrogen atom to which they are attached form a group of the formula

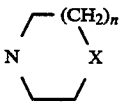

wherein X and n are as above;

(d) $R_6$ and $R_7$ are independently hydrogen, a group of the formula

wherein $R_{20}$ is hydrogen or loweralkyl of 1 to 6 carbon atoms, or a group of the formula

wherein $R_{13}$ is hydrogen, loweralkyl of 1 to 6 carbon atoms, hydroxyloweralkyl of 2 to 6 carbon atoms, loweralkoxyloweralkyl having 1 to 6 carbon atoms in the alkoxy group and 2 to 6 carbon atoms in the alkyl group, a group of the formula $HOCH_2CH(OH)CH_2$; $R_{14}$ is hydrogen, hydroxyl, loweralkoxy of 1 to 6 carbon atoms, loweralkyl of 1 to 6 carbon atoms, hydroxyloweralkyl of 2 to 6 carbon atoms, loweralkoxyloweralkyl of 1 to 6 carbon atoms in the alkoxy group and 2 to 6 carbon atoms in the alkyl group, loweralkanoyl of 2 to 6 carbon atoms, loweralkanoylloweralkyl of 2 to 6 carbon atoms in the alkanoyl group and 1 to 6 carbon atoms in the alkyl group, a group of the formula

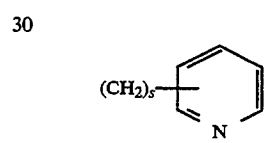

wherein s is 1 or 2, a group of the formula

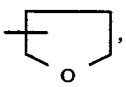

a group of the formula

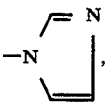

a group of the formula $HOCH_2CH(OH)CH_2$, a group of the formula $(CH_2)_tNR_{21}R_{22}$ wherein $R_{21}$ and $R_{22}$ are independently loweralkyl of 1 to 6 carbon atoms and t is 0, or 2 to 6, $R_{21}$ and $R_{22}$ taken together with the nitrogen atoms to which they are attached form a group of the formula

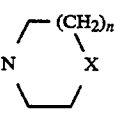

wherein X and n are as above, a group of the formula $OR_{23}$ wherein $R_{23}$ is hydrogen, loweralkyl of 1 to 6 carbon atoms, a group of the formula $(CH_2)_{t'}NR_{21}R_{22}$ wherein t' is 2 to 6, $R_{21}$ and $R_{22}$ are as above, a group of the formula

wherein $R_{24}$ is hydrogen loweralkyl of 1 to 6 carbon atoms, lowercycloalkyl of 3 to 6 carbon atoms, loweralkenyl of 2 to 6 carbon atoms, haloloweralkenyl of 2 to 6 carbon atoms, loweralkanoylloweralkyl of 2 to 6 carbon atoms in the alkanoyl group and 1 to 6 carbon atoms in the alkyl group, loweralkoxyloweralkyl of 1 to 6 carbon atoms in each group, loweralkoxycarbonylloweralkyl of 1 to 6 carbon atoms in each group, loweralkylamino of 1 to 6 carbon atoms, lowerdialkylamino of 2 to 6 carbon atoms, a group of the formula

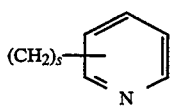

wherein s is as above, a group of the formula

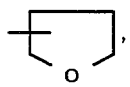

a group of the formula $(CH_2)_t NR_{21}R_{22}$ wherein $R_{21}$, $R_{22}$ and $t'$ are as above, a group of the formula

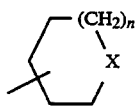

wherein X and n are as above, a group of the formula $(CH_2)_u N(R_{25})COR_{26}$, wherein u is 1, 2 or 3 and $R_{25}$ and $R_{26}$ are independently hydrogen or loweralkyl of 1 to 6 carbon atoms, a group of the formula

wherein $R_{27}$ and $R_{28}$, are loweralkyl of 1 to 6 carbon atoms, with the provisos:

(e) that $R_1$, $R_6$ and $R_7$ are not simultaneously hydrogen, (f) that when $R_1$ and $R_6$ are hydrogen, $R_7$ is not

(g) that $R_6$ and $R_7$ are not simultaneously

(h) that when r is 1, either $R_6$ or $R_7$ is

(i) that when $R_1$ and $R_6$ are hydrogen, $R_{13}$ and $R_{14}$ are not simultaneously loweralkyl of 1 to 6 carbon atoms; and (j) that when $R_1$ and $R_9$ taken together form a group of the formula CO, SO or $CHNR_{11}R_{12}$, $R_6$ and $R_7$ are not simultaneously hydrogen; the optical or geometric isomers thereof, or the pharmaceutically acceptable salts thereof, which are useful for reducing intraocular pressure and treating cardiac failure alone or in combination with inert adjuvants.

Subgeneric to the carbamoyloxylabdanes of the present invention are compounds of formula 1 wherein:

(a) $R_1$ is hydrogen and $R_7$ is a group of the formula

wherein $R_{13}$ and $R_{14}$ are as above;

(b) $R_1$ is hydrogen and $R_6$ is a group of the formula

wherein $R_{13}$ and $R_{14}$ are as above;

(c) $R_1$ is a group of the formula

wherein $R_2$, $R_3$, and r are as above, and $R_6$ and $R_7$ are hydrogen;

(d) $R_1$ and $R_9$ taken together form a group of the formula $CHNR_{11}R_{12}$ wherein $R_{11}$ and $R_{12}$ are as above and $R_6$ or $R_7$ is a group of the formula

wherein $R_{13}$ and $R_{14}$ are as above;

(e) $R_1$ is hydrogen, $R_6$ is hydrogen, $R_{13}$ is hydrogen and $R_{14}$ is loweralkyl of 1 to 6 carbon atoms;

(f) $R_6$ is a group of the formula

wherein $R_{13}$ and $R_{14}$ are as above and $R_7$ is a group of the formula

wherein $R_{20}$ is as above; and (g) $R_7$ is a group of the formula

wherein $R_{13}$ and $R_{14}$ are as above and $R_6$ is a group of the formula

wherein R$_{20}$ is as above.

(h) R$_{13}$ is hydrogen and R$_{14}$ is a group of the formula

wherein R$_{24}$ is loweralkyl of 1 to 6 carbon atoms or a group of the formula

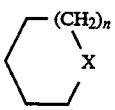

wherein n and X are as above.

As used through the specification and appended claims, the term "alkyl" refers to a straight or branched chain hydrocarbon radical containing no unsaturation and having 1 to 8 carbon atoms such as methyl, ethyl, 1-propyl, 2-propyl, 1-butyl, 1-pentyl, 2-pentyl, 3-hexyl, 4-heptyl, 2-octyl, and the like; the term "alkenyl" refers to a straight or branched chain hydrocarbon radical containing unsaturation in the form of a single carbon to carbon double bond and having from 2 to 8 carbon atoms such as propenyl, 2-butenyl, 2-methyl-2-butenyl, 3-hexenyl, 3-ethyl-2-pentenyl, 3-methyl-3-heptenyl, octenyl, and the like; the term "alkynyl" refers to a straight or branched chain hydrocarbon radical containing unsaturation in the form of a single carbon to carbon triple bond and having from 2 to 8 carbon atoms such as ethynyl, propynyl, 2-butynyl, 3-methylbutynyl, 2-hexynyl, 3-heptynyl, octynyl, and the like; the term "cycloalkyl" refers to a saturated hydrocarbon group possessing at least one carbocyclic ring, the ring containing from 3 to 8 carbon atoms such as cyclopropyl, cyclobutyl, cyclopentyl, cyclohexyl, cyclyheptyl, cyclooctyl, and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, octoxy and the like; the term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, and the like. The term "alkanol" refers to a compound formed by a combination of an alkyl group and a hydroxy radical. Examples of alkanols are methanol, ethanol, 1- and 2-propanol, 1,2-dimethylethanol, hexanol, octanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, and the like; the term "halogen" refers to a member of the family consisting of fluorine, chlorine, bromine or iodine. The term "lower" as applied to any of the aforementioned groups refers to a group having a carbon skeleton containing up to and including 6 carbon atoms.

In the formula presented herein the various substituents are illustrated as joined to the labdane nucleus by one of two notations: a solid line (—) indicating a substituent which is in the β-orientation (i.e., above the plane of the molecule) and a broken line (---) indicating a substituent which is in the α-orientation (i.e, below the plan of the molecule). The formulas have all been drawn to show the compounds in their absolute stereochemical configuration. Inasmuch as the starting materials having a labdane nucleus are naturally occurring or are derived from naturally occurring materials, they, as well as the final products, have a labdane nucleus existing in the single absolute configuration depicted herein. The processes of the present invention, however, are intended to apply as well to the synthesis of labdanes of the racemic series.

In addition to the optical centers of the labdane nucleus, the substituents thereon may also contain chiral centers contributing to the optical properties of the compounds of the present invention and providing a means for the resolution thereof by conventional methods. A wavy line (~) connecting a group to a chiral center indicates that the stereochemistry of the center is unknown, i.e., the group may exist in any of the possible orientations. The present invention comprehends all optical isomers and racemic forms of the compounds of the present invention where such compounds have chiral centers in addition to those of the labdane nucleus.

The novel labdanes of the present invention are synthesized by the processes illustrated in Reaction Schemes A and B.

To prepare a carbamoyloxylabdane 4, an 8,13-epoxy-1α,6β,9α-trihydroxylabd-14-en-11-one-1,9-dialkylformamide acetal 2, the synthesis of which is described in U.S. patent application Ser. No. 848,053, filed Apr. 4, 1986, is carbamoylated to provide a 7β-carbamoyloxylabdaneformamide acetal 3 which is hydrolyzed to a 7β-carbamoyloxy-1α,6β, 9α-trihydroxylabdane 4.

The carbamoylation is accomplished by treating a 6β,7β-dihydroxylabdane 2 with 1,1'-carbonyldiimidazole 8

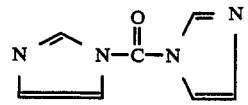

in an alkyl alkanoate or a halocarbon to afford an imidazolocarbonyloxylabdane of formula 9

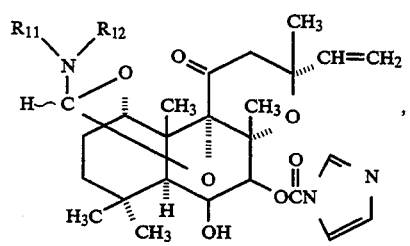

which, preferably without isolation, is treated with an amine of formula 10

wherein R$_{13}$ and R$_{14}$ are as above, neat, in an alkyl alkanoate, halocarbon or a mixture of a halocarbon and an alkanol to yield 4. Among alkyl alkanoates there may be mentioned methyl acetate, ethyl acetate, methyl propionate, ethyl propionate and the like. Ethyl acetate is preferred. Among halocarbons there may be mentioned dichloromethane, trichloromethane and the like. Dichloromethane is preferred. Among alkanols there may be mentioned methanol, ethanol, 2-propanol and the like. Methanol is preferred and mixtures of dichloromethane and methanol are also preferred. While the temperature at which the carbamoylation is performed is not narrowly critical, it is preferred to carry out the reaction at a temperature between about 0° C. to about 50° C., most preferrably at a temperature of about 25° C.

If desired, the intermediate imidazolocarbonyloxylabdane 9 may be isolated by workup of the reaction mixture prior to the addition of amine 10 by methods well-known in the art. For example, the intermediate labdane 9 may be isolated by chromatography on a suitable column (e.g, silica gel) with an appropriate eluent such as hexane/ethyl acetate.

While the relative amounts of 6β,7β-dihydroxylabdane 2 and 1,1'-carbonyldiimidazole 8 are not narrowly critical in the carbamoylation process, i.e., in the conversion of 2 to 4 via a 7-imidazolocarbonyloxylabdane 9, it is desirable to employ about one molar equivalent of each reactant to maximize the formation of the monosubstituted imidazolo precursor 9 of the monosubstituted carbamoyloxylabdane 4. When about two molar equivalents of 1,1'-carbonyldiimidazole 8 to one molar equivalent of 6β,7β-dihydroxylabdane 8 are employed, a 6β,7β-bisimidazolocarbonyloxylabdane 9a is formed.

The hydrolysis is achieved by contacting a 7β-carbamoyloxylabdaneformamide acetal 3 with aqueous alkanol, or with an aqueous alkanoic acid in alkanol, or a mineral acid in aqueous alkanol. Included among aqueous alkanoic acids are aqueous formic acid, aqueous acetic acid, aqueous propionic acid and the like. Included among mineral acids are hydrochloric acid, hydrobromic acid, sulfuric acid, nitric acid and the like. Included among alkanols are methanol, ethanol, 2-propanol and the like. A reaction medium consisting of about 80% aqueous acetic acid and methanol or aqueous methanol is preferred. The hydrolysis proceeds readily at a temperature within the range of about 0° C. to about 50° C. in 80% aqueous acetic acid, and above 40° C. to 90° C. in aqueous methanol. The preferred hydrolysis temperatures in aqueous acetic acid and aqueous methanol are about 25° and 65° C., respectively.

Alternatively, the carbamoylation of a 6β,7β-dihydroxylabdaneformamide acetal 2 is effected by treating such a labdane 2 with a base, for example, an alkali metal bis(trialkylsilyl)amide of formula 11

  11 wherein $R_{17}$ is loweralkyl in an organic solvent, for example, an ethereal solvent, to form an alkali metal alkoxide of 2, followed by treatment with either an isocyanate of formula 12

  12 wherein $R_{13}$ is as hereinbeforedescribed or a carbamoyl halide of formula 13

  13 wherein $R_{13}$ and $R_{14}$ are as hereinbeforedescribed and Hal is halogen, neat or in an ethereal solvent, to provide a 7β-carbamoyloxylabdane 3. Examples of alkali metal bis(trialkylsilyl)amides include lithium, sodium or potassium bis(trimethylsilyl)-or bis(triethylsilyl)amides and the like. Examples of ethereal solvents are diethyl ether, 1,2-dimethoxyethane, dioxane, tetrahydrofuran and the like. A reaction medium consisting of lithium bis(trimethyl)silylamide and tetrahydrofuran is preferred. The formation of the alkali metal alkoxide is performed at a temperature within the non-critical range of about −25° C. to about 50° C., preferably at a temperature of about 0° C. to about 25° C. The condensation of an alkali metal alkoxide of 2 with either an isocyanate 12 or a carbamoyl halide 13 is performed at a temperature of about 0° C. to about the reflux temperature of the reaction medium, preferrably at about 25° C. to the reflux temperature.

To prepare a 6β-carbamoyloxylabdane of formula 5, a 7β-carbamoylabdane of formula 4 is rearranged by means of an alkali metal alkoxide in an alkanol or ethereal solvent, alone or combination, at a temperature within the range of about 0° C. to about 50° C., a temperature of about 25° C. being preferred. Suitable alkali metal alkoxides include lithium, sodium and potassium 2-propoxides, lithium, sodium and potassium 2,2-dimethylethoxides and the like. Suitable alkanols include 2-propanol, 2,2-dimethylethanol and the like. Suitable ethereal solvents include diethyl ether, 1,2-dimethoxyethane, tetrahydrofuran, dioxane and the like. Potassium 2,2-dimethylethoxide and a combination of 2,2-dimethylethanol and tetrahydrofuran is the preferred rearrangement medium.

To prepare a carbamoyloxy-6β,7β,9α-trihydroxylabdane of formula 7, 8,13-epoxy-1α,6β,7β,9α-tetrahydroxylab-14-en-11-one 6, the synthesis of which is described in U.S. Pat. No. 4,134,986, issued Jan. 16, 1979 to B. S. Bajwa, et al., is contacted with 1,1'-carbonyldiimidazole 8 in an ethereal solvent such as tetrahydrofuran followed by an amine 10 wherein $R_{13}$ and $R_{14}$ are $R_2$ and $R_3$, respectively, under conditions substantially similar to those employed for the conversion of 6β,7β-dihydroxylabdane-1β,9β-formamide acetal 2 to a 7β-carbamoyloxylabdane 3, as hereinbeforedescribed.

To construct a carbamoyloxylabdane having a 1α,9α-sulfite or carbonate function, i.e., a compound of formula 15 wherein $R_{13}$ and $R_{14}$ are as above and Y is SO or CO, an 8,13-epoxy-1α,6β,7β,9α-tetrahydroxylabdane-14-en-11-one1α,9α-sulfite or -carbonate 14, the preparation of which is described in by N. J. de Souza, et al., Medicinal Research Reviews, 3, 201 (1983), may be treated with 1,1'-carbonyldiimidazole 8 followed by an amine of formula 10, or an alkoxide of 13 may be condensed with an isocyanate 12 or carbamoyl halide 13, all steps being performed by processes substantially similar to those described herein for the related conversion of 7β-hydroxylabdane 2 to 7-carbamoyloxylabdane 3.

Similarly, to fabricate a carbamoyloxy labdane characterized by the presence of a 1α,9α-sulfite function and, for example, a 7β-(N-alkanoylaminocarbonyloxy) group, a 7β-aminocarbonyloxy-1β,9β-dihydroxylabdane 4wherein $R_{13}$ and $R_{14}$ are hydrogen is converted to a 7β-aminocarbonyloxy-1α,9α-dihydroxy-1α,9α-sulfite 15 which is condensed with an alkanoic acid anhydride of formula 19

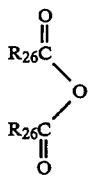   19 wherein $R_{26}$ is alkyl to a 7β-(N-alkanoylaminocarbonyloxy)-1α,9α-dihydroxylabdane-1α,9α-sulfite 17. See Reaction Scheme C.

The introduction of the 1α,9α-sulfite is accomplished by treating a 1α,9α-dihydroxylabdane 4 with thionyl chloride 8in the presence of pyridine or a tertiary amine and an inert solvent. Among tertiary amines, there may be mentioned trialkylamines such as trimethylamine, triethylamine, tripropylamine and the like, and heteroaromatic amines such as pyridine, picoline, lutidine, collidine and the like. Trialkylamines are preferred. Triethylamine is most preferred. Among inert solvents, there may be mentioned halocarbons such as dichloromethane, trichloromethane, 1,1- and 1,2-dichloroethane and the like. Dichloromethane is preferred. While the reaction temperature at which the sulfite introduction is performed is not critical, it is preferred to conduct the reaction at a temperature of about 10° to about 40° C., a reaction temperature of about 25° C. being most preferred.

The condensation is effected by contacting a 7β-(aminocarbonyloxy)labdane 17 with an anhydride 19 in the presence of a mineral acid or a sulfonic acid. Included among mineral acids are sulfuric acid, nitric acid, hydrochloric acid and the like. Included among sulfonic acids are methanesulfonic acid, hexanesulfonic acid, p-toluenesulfonic acid and the like. Mineral acids are preferred. Sulfuric acid is most preferred. The condensation is preferably performed at about 25° C. Reduced or elevated temperature, however, in the range of about 10° C. to about 40° C. may be employed.

To gain entry into the labdane series characterized by the presence of a 7β-(N-alkanoylaminocarbonyloxy) function and a 1α,9α-dihydroxy moiety, i.e., a compound of formula 18, a 7β-(N-alkanoylaminocarbonyloxy)-1α,6β,9α-trihydroxylabd-14-en-11-one 17-1,9-carbonate is subjected to hydrolylic processes. Hydrolysis, for example, is achieved by contacting a 1α,-9α-carbonate 17 with water in an appropriate solvent such as pyridine, picoline, lutidine, collidine and the like, pyridine being preferred. The hydrolysis is generally conducted at the reflux temperature of the reaction medium. It may, however be performed at temperatures from room temperature to the reflux temperature of the medium.

To introduce an N-(alkylaminoalkylcarbonyloxy) function at the 1α-position of the labdane nucleus, i.e., to prepare for example, a labdane of formula 21 wherein $R_2, R_3, R_{13}, R_{14}$, and r are as hereinbeforedefined, a 7β-carbamoyloxy-1α-hydroxylabane 4 is acylated to a 1α-haloacetoxy-7β-carbamoyloxylabdane 20 which is aminated to 21. See Reaction Scheme D.

The acylation utilizing a haloalkylalkanoyl halide of formula 22

   22 wherein r is 1 and Hal is chloro, bromo or iodo is conducted in the presence of a dialkylaniline such as dimethylaniline, diethylaniline and the like in a halocarbon such as dichloromethane, trichloromethane, 1,1- or 1,2-dichloroethane, 1,1- or 1,2-dichloroethylene and the like at a reaction temperature from about 0° to about 50° C. Dimethylanine and dichloromethane is the preferred reaction medium. A temperature within the range from about 0° to about 25° C. is the preferred reaction temperature. The 1α-haloalkylcarbonyloxylabdane 20 is isolated by conventional work-up of the reaction mixture, e.g., extraction and evaporation.

The amination is accomplished by contacting a 1α-haloalkylcarbonyloxylabdane 20 with an alkylamine of formula 23

$R_2R_3NH$   23 wherein $R_2$ and $R_3$ are as hereinbeforedisclosed in an alkyl alkanoate at a temperature from about 5° to about 55° C., a reaction temperature of about 25° C. being preferred. Included among alkyl alkanoates are methyl acetate, ethyl acetate, methyl propionate, ethyl propionate and the like. Ethyl acetate is the preferred alkyl alkanoate.

To synthesize a 7β-(N-acyloxyaminocarbonyloxy)-labdane of formula 25, a 7β-(N-hydroxyaminocarbonyloxy)labdane 24 is condensed with a carboxylic acid of formula 26

   26 wherein $R_{18}$ is as hereinbeforedefined in the presence of 1,1'-carbonyldiimidazole 8 in a halocarbon such as dichloromethane, trichloromethane, 1,1- or 1,2-dichloroethane, 1,1- or 1,2-dichloroethylene and the like, or an alkyl alkanoate such as methyl acetate, ethyl acetate, methyl propionate, ethyl propionate and the like at a reaction temperature within the range of about 5° to about 50° C. The preferred solvents are dichloromethane and ethyl acetate. An ethereal cosolvent, e.g. tetrahydrofuran, dioxane, diethyl ether, dimethoxyethane and the like may be employed when a halocarbon is used as the reaction medium. Tetrahydrofuran is the preferred cosolvent. The preferred reaction temperature is about 25° C. In the event, an amino acid 26 in the form of its hydrohalide salt, i.e., an amino acid wherein $R_{18}$ is characterized by the presence of a basic amine function is utilized as a reactant, an acid acceptor such as, for example, a trialkylamine is also employed in the reaction medium. Included among trialkylamines are trimethylamine, triethylamine, tripropylamine and the like. Triethylamine is the preferred acid acceptor.

A carbodiimide of formula 27

   27 wherein $R_{28}$ is dialkylaminoalkyl and $R_{29}$ is alkyl may be employed as the condensing agent instead of the carbonylimidazole 8 in the process for the conversion of 24 to 25. An acid acceptor, e.g., a 4-dialkylaminopyridine such as 4-dialkylaminopyridine is utilized when a hydrohalide salt of carbodiimide 27 is employed as a the condensing agent.

In the alternative, a 7β-(N-acyloxyaminocarbonyloxy)labdane 25 is prepared from a 7β-(N-hydroxyaminocarbonyloxy)labdane 24 by the mixed anhydride method. For example, treatment 8,13-epoxy, 7β-(hydroxyaminocarbonyloxy)-1α,6β,9α-trihydroxylabd-14-en-11-one 24 wherein $R_1$ and $R_{13}$ are hydrogen with the mixed anhydride of acrylic acid or methylacylic acid and 2,2-dimethylpropionic acid of formulas 28 or 28a

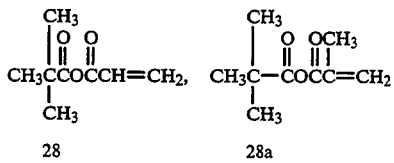

28          28a prepared, in situ, by contacting acrylic acid with 2,2-dimethylpropionyl chloride in the presence of triethylamine as an acid acceptor and dichloromethane as the reaction solvent, in dichloromethane containing tetrahydrofuran as a cosolvent and 4-dimethylaminopyridine as an acid scavenger and/or catalyst affords 7β-(N-acryloyloxyaminocarbonyloxy)-8,11-epoxy-1α,6β,9α-trihydroxylabd-14-en11-one 25 wherein $R_1$ is hydrogen, $R_{13}$ is hydrogen and $R_{24}$ is acrylyl.

A 7β-(N-carbamoylaminocarbonyloxy) labdane, for example, a labdane of formula 25 wherein $R_{24}$ is dialkylamino, more particularly dimethylamino, is elaborated by the carbamoyl halide method. Thus, treatment of a 7β-(N-hydroxyaminocarbonyloxy)labdane 24 with an N,N-dialkylcarbamoyl halide of formula 29

29 wherein $R_{30}$ and $R_{31}$ are alkyl and Hal is chloro, bromo or iodo, more particularly N,N-dimethylcarbamoyl chloride, i.e., a compound of formula 29 wherein $R_{30}$ and $R_{31}$ are dimethyl and Hal is chloro, in a halocarbon such as, for example, dichloromethane, and an acid acceptor such as, for example, triethylamine, provides a 7-substituted labdane wherein $R_{24}$ is N,N-dialkyl, more particularly, N,N-dimethyl.

To prepare a labdane substituted at the 7-position by an (alkylcarbonylalkyl)aminocarbonyloxy function, i.e., to prepare a compound of formula 1 wherein $R_{14}$ is alkanoylalkyl, an appropriate secondary carbinol, for example, a compound of formula 30 wherein $R_1$ and $R_9$ taken together form a group of the formula $CHNR_{11}R_{12}$ wherein $R_{11}$ and $R_{12}$ are as hereinbeforedefined is oxidized by the oxalyl chloride-dimethylsulfoxide complex in the presence of an acid acceptor such as triethylamine at a reduced temperature within the range of about −60° to about −50° C. to afford a 7β-[N-(2-oxopropyl)aminocarbonyloxy]labdane 31 wherein $R_1$ and $R_9$ are as above. The 1α,9α-dimethylformamide acetal protecting group is cleaved by hydrolysis processes hereinbeforedescribed to provide the 1α9α-dihydroxylabdane substituted at the 7β-position by the aforesaid carbonyloxy group, i.e., a compound of formula 31 wherein $R_1$ and $R_9$ are hydrogen.

To introduce an aminocarbonyloxy function at the 6-position of the labdane nucleus, i.e., to prepare, for example,. a compound of formula 34, a labdane-formamide acetal 32 ($R_1$ and $R_9$ taken together form a group of the formula $CHNR_2R_3$ where $R_2$ and $R_3$ are alkyl) is acylated with diimidazole 8 in the presence of an amine 10 to provide a 6β-aminocarbonyloxylabdanedialkylformamide acetal 34 ($R_1$ and $R_9$ form a group of the formula $CHNR_2R_3$ wherein $R_2$ and $R_3$ are alkyl) which is hydrolyzed to a 6β-aminocarbonyloxy-1α,7β,9α-trihydroxylabane 34 wherein $R_1$ and $R_9$ are hydrogen. The acylation is carried out by treating 32 with diimidazole 8 in a halocarbon such as, e,g., dichloromethane, trichloromethane, tetrachloromethane, 1,1- or 1,2-dichloroethane, 1,1- or 1,2-dichloroethylene and the like, an alkyl alkanoate such as, e.g., methyl acetate, ethyl acetate, ethyl propionate and the like, or an ethereal solvent such as, e.g. tetrahydrofuran, dioxane, diethyl ether and the like, in the presence of a tertiary amine such as e.g., a trialkylamine (i.e., trimethylamine, triethylamine, tripropylamine, lutidine, collidine or the like, or a heteroaromatic amine such as, e.g. pyridine, picoline and the like, followed by an amine 10 at a reaction temperature of from about 0° C. to the reflux temperature of the solvent system. The preferred solvent is a halocarbon, dichloromethane being most preferred. The preferred reaction temperature is about 25° C.

To promote formation of the 6β-carbamoyloxylabdane 34, the initial stage of the conversion of 32 to 34, i.e., the treatment of 32 with diimidazole 8 in the presence of a tertiary amine is allowed to proceed for an extended period of time, preferably for about 12 to about 36 hours, most preferably for about 24 hours. The intermediate 6β,7β-dihydroxylabdane-6β,7β-carbonate 33 is isolated and, in turn, treated with amine 10 to form 6β-carbamoyloxylabdane 34, or the conversion may be conducted in situ, preferably in situ.

A 6β-carbamoyloxy-7β-hydroxylabdane 34 (wherein $R_1$ and $R_9$ together are $CHNR_{11}R_{12}$ wherein $R_{11}$ and $R_{12}$ are alkyl) may be acylated to a 7β-alkanoyloxy-6β-carbamoyllabdane 35 (wherein $R_1$ and $R_9$ together are $CHNR_{11}R_{12}$ wherein $R_{11}$ and $R_{12}$ are alkyl) by, for example, an alkanoic acid anhydride 19 such as acetic acid anhydride 19 (wherein $R_{26}$ is methyl) in an alkanoic acid such as acetic acid 26 (wherein $R_{18}$ is methyl) in the presence of a tertiary amine such as 4-dimethylaminopyridine to provide a 7β-alkanoyloxy-6β-carbamoyloxylabdane 35 (wherein $R_1$ and $R_9$ are as above) such as a 7β-acetoxy-6β-carbamoyloxylabdane 35 (such as a 7β-acetoxy-6β-carbamoyloxylabdane 35 (wherein $R_1$ and $R_9$ are as above).

A 6β-alkanoyloxy-7β-hydroxylabdane 37 (wherein $R_1$ and $R_9$ taken together are $CHNR_{11}R_{12}$ wherein $R_{11}$ and $R_{12}$ are alkyl), the preparation of which is described in U.S. patent application Ser. No. 849,053, now U.S. Pat. No. 4,639,443, granted Jan. 27, 1987, may be carbamoylated to a 6β-alkanoyloxy-7β-carbamoyloxy labdane 38 (wherein $R_1$ and $R_9$ are as above) by, for example, the procedure hereinbeforedescribed for the conversion 2 to 3.

By following the hydrolytic processes hereinbeforedescribed for the cleavage of the 1α,9α-dihydroxy-1α,9α-dialkylformamide acetal group, a 6β-carbamoyloxylabdane 34 wherein $R_1$ and $R_9$ together are $CHNR_{11}R_{12}$ wherein $R_{11}$ and $R_{12}$ are alkyl is converted to a 6β-carbamoyloxy-1α,9α-dihydroxylabdane 34 wherein $R_1$ and $R_9$ are hydrogen.

Similarly, by following these hydrolytic processes, the 1α,9α-dihydroxy-1α,9α-dialkylformamide acetal group of 7β-alkoxy-6β-carbamoyloxylabdane 35 (wherein $R_1$ and $R_9$ together are $CHNR_{11}R_{12}$ wherein $R_{11}$ and $R_{12}$ are alkyl) may be cleaved to the corresponding 1α,9α-dihydroxy derivatives 35 and 36 (wherein $R_1$ and $R_9$ are hydrogen) (see Reaction Schemes E and F). A reduced hydrolysis temperature of about 25° C. may be employed.

The carbamoyloxylabdanes of the present invention are useful in the treatment of glaucoma by virtue of their ability to reduce elevated intraocular pressure in a glaucomatous subject as determined by the method described by J. Caprioil, et al., *Invest. Ophthalmol. Vis. Sci.*, 25, 268 (1984). The results of the determination expressed as percent decrease of outflow pressure is presented in Table I.

TABLE I

| COMPOUND | CONCENTRATION (%) | DECREASE IN OUTFLOW PRESSURE |
|---|---|---|
| 8,13-epoxy-7β-(N-methyl-aminocarbonyloxy)-1α, 6β, 9α-trihydroxylabd-14-en-11-one | 0.25 | 59 |
| 7β-(aminocarbonyl-oxy)-8,13-epoxy-1α-6β, 9α-trihydroxylabd-14-en-11-one | 0.50 | 41 |
| 8,13-epoxy-7β-(2-hydroxyethylamino-carbonyloxy)-1α, 6β, 9α-trihydroxylabd-14-en-11-one | 0.25 | 50 |
| 7β-acetoxy-8,13-epoxy-1α, 6β, 9α-trihydroxylabd-14-en-11-one | 1.0 | 51 |
|  | 0.1 | 23 |

Intraocular pressure reduction is achieved when the present carbamoyloxylabdanes are administered to a subject requiring such treatment as an effective topical dose of a 0.01 to 3.0% solution or suspension. A particularly effective amount is about 3 drops of a 0.25% preparation per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The carbamoyloxylabdanes of the present invention are also useful in the treatment of cardiac failure by virtue of their ability to elicit a positive ionotropic effect as evidenced by an increase in contractile force in an isolated guinea pig atria assay, the electrically-driven guinea pig left atrium assay, which is performed as follows:

Male guinea pigs weighing 200-300 grams are stunned with a blow to the back of the head. The heart is rapidly removed and placed in a petri dish containing Krebs solution. The ventricle is separated from the atria, the atria are sectioned into the right and left atria and double-O silk ligatures are tied to the apex of the left atrium. The atrium is fixed to a pair of platinum plate electrodes and suspended in a 20-ml tissue bath containing Kreb's solution aerated with 95% oxygen-5% carbon dioxide at 37° C. One end of the atrium is fixed to a hook in the electrode and the other end is connected to a Grass FTO3 force displacement transducer. Resting tension and stabilization time are the same as described above. The atrium is stimulated at 3 Hz, 0.5 msec duration at supramaximal voltage (constant current) via a Grass S88 stimulator and constant current unit. Force of contraction is continuously displaced on a Gould recorder. Test drug is prepared as in section A and is added to the tissue baths in the same fashion. Change in contractile force from baseline is determined for each concentration, and the change in contractile force (g) is plotted against accumulated drug concentration (ug/ml). The activity of the test drug, i.e., the increase in contractile force (g) from the stabilized force expressed the percentage change at a given concentration is determined graphically, as is the $ED_{50}$-value, i.e., the extrapolated dose (ug/ml) which increases the contractile force by 50% over the stabilized rate.

Results obtained in these assays for representative carbamoyllabdanes and a reference compound as presented in Table II.

TABLE II

| COMPOUND | CONC (g/ml) | IONOTROPIC ACTIVITY CHANGE (%) OF CONTRACTILE FORCE (g) |
|---|---|---|
| 8,13-epoxy-7β-(N-2,2-(dimethylpropionyloxy)amino-carbonyloxy) - 1α, 6β, 9α-trihydroxylabd-4-en-11-one | 0.414[1] | 50 |
| 8,13-eppxy-7β-[N-propionyloxyamino-carbonyloxy)-1α, 6β,-9α-trihydroxylabd-4-en-11-one | 0.28[1] | 50 |
| 8,13-epoxy-7β-[N-(1-methylpiperidino-carbonyloxyl]-1α, 6β,-9β-trihydroxylabd-4-en-11-one | 0.046[1] | 50 |
| 8,13-epoxy-7β-[N-(3-hydroxypropyl) - aminocarbonyloxyl]-1α, 6β, 9α-trihydroxy-labd-14-en-11-one | 0.058[1] | 50 |
| 7β-acetoxy-8,13-epoxy-1α, 6β, 9β-trihydroxylabd-14-en-11-one | 0.073[1] | 50 |

[1]extrapolated $ED_{50}$-value

Cardiac failure treatment is achieved when the present carbamoyloxylabdanes are administered to a subject requiring such treatment as an effective oral, parenteral or intravenous dose of 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosage set forth herein are examplary only and that they do not, to any extent, limit the scope or practice of the invention.

Compounds of the present invention include:
(a) 1α-(Aminocarboxyloxy)-8,13-epoxy-6β,7β,9α-trihydroxylabd-14-en-11-one;
(b) 8,13-Epoxy-1α-(N-methylaminocarbonyloxy)-6β,7β,9α-trihydroxylabd-14-en-11-one;
(c) 8,13-Epoxy-1α-(4-morpholinocarbonyloxy)6β,9α-trihydroxylabd-14-en-11-one;

(d) 8,13-Epoxy-1α-(4-thiomorpholinocarbonyloxy)-6β,7β,9α-trihydroxylabd-14-en-11-one;

(e) 8,13-Epoxy-1β-(4-hydroxy-1-piperidinocarbonyloxy)-6β,7β9α-trihydroxylabd-14-en-11-one;

(f) 8,13-Epoxy-1α-(4-acetoxy-1-piperidinocarbonyloxy)-6β,7β,9α-trihydroxylabd-14-en-11-one;

(g) 8,13-Epoxy-1α-(4-acetoxy-1-piperidinocarbonyloxy)-6β,7β,9α-trihydroxylabd-14-en-1-one;

(h) 8,13-Epoxy-7β-(4-thiomorpholinocarbonyloxy)-1α,6β,9α-trihydroxylabd-14-en-11-one-1,9-carbonate;

(i) 8,13-Epoxy-7β-(4-methoxy-1-piperidinocarbonyloxy)-1α,6β,9α-trihydroxylabd-14-en-11-one-1,9-sulfite;

(j) 8,13-Epoxy-6β-(4-thiomorpholinocarbonyloxy)-1α,7β,9α-trihydroxylabd-14-en-11-one-1,9-(4-thiomorpholine)formamide acetal;

(k) 8,13-Epoxy-7β-(4-methoxy-1-piperidinocarbonyloxy)-1α,6β,9α-trihydroxylabd-14-en-11-one-1,9-(4-morpholino)formamide acetal;

(l) 8,13-Epoxy-7β-(4-acetoxy-1-piperidinocarbonyloxy)-1α,6β,9α-trihydroxylabd-14-en-11-one-1,9-(4-acetoxy-1-piperidine)formamide acetal;

(m) 7β-[2-(2-Dimethylaminoethyl)aminocarbonyloxy]-8,13-epoxy-1α,6β,9α-trihydroxylabd-14-en-11-one;

(n) 7β-[N-(3-Dimethylaminopropyl)aminocarbonyloxy]-8,13-epoxy-1α,6β,9α-trihydroxylaba-14-en-11-one-1,9-dimethylformamide acetal;

(o) 7β-[N-(3-Dimethylaminopropyl)aminocarbonyloxy]-8,13-epoxy-1α,6β,9α-trihydroxylabd-14-en-11-one:

(p) 7β-[N-(3-Dimethylaminopropionyloxy)aminocarbonyloxy]-8,13-epoxy-1α,6β,9α-trihydroxylabd-14-en-11-one-1,9-dimethylformamide acetal;

(q) 7β-[N-(3-Dimethylaminobutynyloxy)aminocarbonyloxy]-8,13-epoxy-1α,6β,9α-trihydroxylabd-14-en-11-one;

(r) 7β-[N-(4-Dimethylaminobutynyloxy)aminocarbonyloxy]-8,13-epoxy-1α,6β,9α-trihydroxylabd-14-en11-one-1,9-dimethylformamide acetal;

(s) 7β-(N-dimethylaminoacetoxy)aminocarbonyloxy-8,13-epoxy-1α,6β,9α-trihydroxylabd-14-en-11-one-1,9-dimethylformamide acetal;

(t) 7β-(N-dimethylaminoacetoxy)aminocarbonyloxy-8,13-epoxy-1α,6β,9α-trihydroxylabd-14-en-11-one;

(u) 8,13-Epoxy-7β-[N-(4-methylpiperazinylcarbonyloxy)aminocarbonyloxy]-1α,6β,9α-trihydroxylabd-14-en-11-one-1,9-dimethylformamide acetal;

(v) 8,13-Epoxy-7β-[N-(4-methylpiperazinylcarbonyloxy)aminocarbonyloxy]-1α,6β,9α-trihydroxylabd-14-en-11-one;

(w) 8,13-Epoxy-7β-[N-(2-morpholinoethyl)aminocarbonyloxy]-1α,6β,9α-trihydroxylabd-14-en-11-one;

(x) 8,13-Epoxy-7β-[N-(2-morpholinoethyl)aminocarbonyloxy]-2α,6β,9α-trihydroxylabd-14-en-11-one-1,9-dimethylformamide acetal;

(y) 7β-[N-(2-Dimethylaminoethylaminocarbonyloxy)aminocarbonyloxy]-8,13-epoxy-1α,6β,9α-trihydroxylabd-14-en-11-one-1,9-dimethylformamide acetal;

(z) 7β-[N-(2-Dimethylaminoethylaminocarbonyloxy)aminocarbonyloxy]-8,13-epoxy-1α,6β,9α-trihydroxylabd-14-en-11-one;

(a') 8,13-Epoxy-6β-(N-propionyloxyaminocarbonyloxy)-1α,7β,9α-trihydroxylabd-14-en-11-one-1,9-dimethylformamide acetal;

(b') 8,13-Epoxy-6β-(N-propionyloxyaminocarbonyloxy)-1α,7β,9α-trihydroxylabd-14-en-11-one;

(c') 8,13-Epoxy-7β-(N-methylaminoacetoxyaminocarbonyloxy)-1α,6β,9α-trihydroxylabd-14-en-11-one;

(d') 6β-Acetoxy-8,13-epoxy-7β-[(N-3-(dimethylaminopropyl)aminocarbonyloxy]-1α,9α-dihydroxylabd-14-en-11-one; and (e') 7β-Acetoxy-8,13-epoxy-6β-[N-3-(dimethylaminopropyl)aminocarbonyloxy]-1α,9α-dihydroxylabd-14-en-11-one.

The carbamoyloxylabdanes of the present invention are also useful in the treatment of hypertension, congestive heart failure, bronchial asthma and psoriasis.

Effective amounts of the compounds of the present invention may be administered to a subject by any one of various methods, for example, orally as in capsules or tablets, parenterally in the form of sterile solutions or suspensions, in some cases intravenously in the form of sterile solutions, or suspensions, and topically in the form of solutions, suspensions or ointments and by aerosol spray.

Effective quantities of the compounds of the invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 0.1-30 milligrams of the active compound.

The tablets, pills, capsules, troches and the like may also contain the following ingredients: a binder such as microcrystalline cellulose, gum tragacanth or gelatin an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of oral, parenteral or topical therapeutic administration, the active compounds of the invention may be incorporated into a solution, suspension, ointment or cream. These preparations should contain at least 0.01% of active compound, but may be varied between 0.1 and about 5% of the weight thereof. The amount of active compounds in such compositions is such that a suitable dosage will be obtained. Preferred compositions and preparations according to the present invention are prepared so that a parenteral or topical dosage unit contains between 0.01 to 10 milligrams of active compound.

The solutions or suspensions for topical or parenteral administration may also include the following components: sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phophates and agents for the adjustment of tonicity such as sodium chloride or dextrose. The parenteral preparation can be enclosed in ampules or disposable syringes; the topical preparation may be enclosed in multiple dose vials or dropping bottles, made of glass or plastic.

The compounds of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic, carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

The following Examples are for illustrative purposes only. All temperatures are given in degrees Centigrade.

EXAMPLE 1

7$\beta$-(Aminocarbonyloxy)-8,13-epoxy-1$\alpha$,6$\beta$,9$\alpha$-trihydroxylabd-14-en-11-one-1,9-dimethylformamide acetal A solution of 484 mg of 8,13-epoxy-1$\alpha$,6$\beta$,7$\beta$,9$\alpha$-tetrahydrolabd-14-en-11-one-1,9-dimethylformamide acetal in 10 ml of ethyl acetate containing 202.5 mg of 1,1'-carbonyldiimidazole was stirred at ambient temperature overnight. Anhydrous ammonia was bubbled into the mixture for 1 min and the mixture was stirred at ambient temperature for 48 to 72 hr in a sealed vessel. The mixture was filtered and evaporated. The residue was flash chromatographed on silica gel in hexane:ethyl acetate (1:1). The appropriate fractions were combined and evaporated. The residue was recrystallized from hexane:ether to afford 148 mg (26.9%) of product, mp 98°–122°.

ANALYSIS:
Calculated for $C_{24}H_{38}N_2O_7$: 61.77%C, 8.23%H, 6.00%N,
Found: 61.73%C, 8.42%H, 5.49%N

EXAMPLE 2

8,13-Epoxy-7$\beta$-(N-methylaminocarbonyloxy)-1$\alpha$,6$\beta$,9$\alpha$-trihydroxylabd-14-en-11-one-1,9-dimethylformamide acetal To a solution of 100 mg of 8,13-epoxy-1$\alpha$,6$\beta$,7$\beta$,9$\alpha$-tetrahydroxylabd-14-en-11-one-1,9-dimethylformamide acetal in 10 ml of tetrahydrofuran was added 23 $\mu$l of a 1 M solution of lithium bis(trimethylsilyl)amide in tetrahydrofuran. Methyl isocyanate (14 $\mu$l, 13.5 mg) was added to the mixture and the mixture was stirred at ambient temperature under nitrogen overnight. The mixture was quenched with 100 $\mu$l of water and evaporated. The residue was flash chromatographed on silica gel in hexane:ethyl acetate (1:1). The appropriate fractions were combined and evaporated to yield 30 mg (26.4%) of product, mp 189°–191°.

ANALYSIS:
Calculated for $C_{25}H_{40}N_2O_7$: 62.47%C, 8.41%H, 5.83%N,
Found: 62.59%C, 8.44%H, 5.65%N

EXAMPLE 3

8,13-Epoxy-7$\beta$-(4-morpholinocarbonyloxy)-1$\alpha$,6$\beta$,9$\alpha$-trihydroxylabd14-en-11-one-1,9-dimethylformamide acetal A solution of 500 mg of 8,13-epoxy-1$\alpha$,6$\beta$,7$\alpha$-9$\alpha$-tetrahydroxylabd-14-en-11-one-1,9-dimethylformamide acetal in 10 ml of ethyl acetate containing 202.5 mg of 1,1'-carbonyldiimidazole was stirred at ambient temperature under nitrogen over the weekend. Morpholine (500 ml) was added and the mixture was stirred ambient temperature for 24 hr. The mixture was diluted with 100 ml of ethyl acetate and washed with 0.01 N hydrochloric acid until the aqueous washings remained acidic. The organic phase was washed with saturated aqueous sodium bicarbonate solution, dried over anhydrous sodium sulfate, filtered and evaporated. The residue was flash chromatographed on silica gel in hexane:ethyl acetate (1:1). The appropriate fractions were combined and evaporated to yield 180 mg (27.3%) of product, mp 75°–100°.

ANALYSIS:
Calculated for $C_{28}H_{44}N_2O_5$: 62.65%C, 8.28%H, 5.22%N,
Found: 62.60%C, 8.34%H, 5.07%N

EXAMPLE 4

8,13-Epoxy-7$\beta$-(4-hydroxy-1-piperidinocarbonyloxy)-1$\alpha$,6$\beta$,9$\alpha$-trihydroxylabd-14-en-11one-1,9-dimethylformamide acetal A solution of 500 mg of 8,13-epoxy-1$\alpha$,6$\beta$,7$\beta$,9$\alpha$-tetrahydroxylabd-14-en-11-one-1,9-dimethylformamide acetal in 10 ml of ethyl acetate containing 202.5 mg of 1,1'-carbonyldiimidazole was stirred at ambient temperature under nitrogen for 48 to 72 hr. 4-Hydroxypiperidine (505 mg) was added and the mixture was stirred at ambient temperature for 24 hr. The mixture was diluted with 100 ml of ethyl acetate and washed with 0.1 N hydrochloric acid until the aqueous washings remained acidic. The organic layer was washed with saturated aqueous sodium bicarbonate solution, dried over anhydrous sodium sulfate, filtered and evaporated. The residue was flash chromatographed on silica gel in hexane:ethyl acetate (1:2). The appropriate fractions were combined and evaporated to yield 342.5 mg (51.9%) of product, mp 70°–100°.

ANALYSIS:
Calculated for $C_{29}H_{46}N_2O_8$: 63.24%C, 8.44%H, 5.08%N,
Found: 63.23%C, 8.50%H, 4.99%N

EXAMPLE 5

8,13-Epoxy-7$\beta$-(2-hydroxyethylaminocarbonyloxy)-1$\alpha$,6$\beta$,9$\alpha$-trihydroxylabd-14-en-11-one-1,9-dimethylformamide acetal A solution of 1.5 g of 8,13-epoxy-1$\alpha$,6$\beta$,7$\beta$,9$\alpha$-tetrahydroxylabd-14-en-11-one-1,9-dimethylformamide acetal in 30 ml of ethyl acetate containing 607.5 mg of 1,1'-carbonyldiimidazole was stirred under nitrogen at ambient temperature for 24 hr. A 10 ml-portion of this mixture was combined with a solution of 359.9 mg of 2-aminoethanol in 1 ml of ethyl acetate, and the resultant mixture was stirred for 2 days. The mixture was diluted with ethyl acetate to 100 ml and extracted several times with 0.01 N hydrochloric acid until the aqueous washings remained acidic. The ethyl acetate layer was washed with saturated aqueous sodium bicarbonate solution, dried over anhydrous sodium sulfate, filtered and evaporated. The residue was flash chromatographed on silica gel in hexane:ethyl acetate:methanol (10:10:1). The appropriate fractions were combined and evaporated and the residue was crystallized from hexane:ether to afford 201.3 mg (33.4%) of product, mp 100°–110°.
ANALYSIS:
Calculated for $C_{26}H_{42}N_2O_8$: 61.15%C, 8.31%H, 5.48%N, Found: 60.77%C, 8.34%H, 5.20%N

EXAMPLE 6

7β-(2,3-Dihydroxypropylaminocarbonyloxy)-8,13-epoxy-1α,6β,9α-trihydroxylabd-14-en-11-one-1,9-dimethylformamide acetal A solution of 1.5 g of 8,13-epoxy-1α,6β,7β,9α -tetrahydroxylabd-14-en-11-one-1,9-dimethylformamide acetal was dissolved in 30 ml of ethyl acetate containing 607.5 mg of 1,1′-carbonyldiimidazole and stirred under nitrogen at ambient temperature for 24 hr. A 10 ml-portion of this mixture was combined with a solution of 536.9 mg of 2,3-dihydroxypropylamine in 1 ml of ethyl acetate and the resultant mixture was stirred for 2 days. The reaction mixture was diluted with ethyl acetate to 100 ml and extracted with 0.01 N hydrochloric acid until the aqueous washings remained acidic. The organic phase was washed with saturated aqueous sodium bicarbonate solution, dried over anhydrous sodium sulfate, filtered and evaporated. The residue was flash chromatographed on silica gel in hexane:ethyl acetate:methanol (10:10:1). The appropriate fractions were combined and evaporated. The residue was crystallized from hexane:ether to afford 189.6 mg (29.8%) of product, mp 90°–100°.
ANALYSIS:
Calculated for $C_{27}H_{44}N_2O_9$: 59.97%C, 8.22%H, 5.18%N,
Found: 59.72%C, 8.20%H, 4.97%N

EXAMPLE 7

7β-(N,N-Dimethylcarbamoyloxy)-8,13,-epoxy-1α,6β,-9α-trihydroxylabd-14-en-11-one-1,9-dimethylformamide acetal 8,13-Epoxy-1α,6β,7β,9α-tetrahydroxylabd-14-en-11-one-1,9-dimethylformamide acetal (500 mg) was dissolved in 50 ml of dry tetrahydrofuran under nitrogen and cooled to 0° in an ice-bath. Lithium bis(trimethylsilyl)amide (1.4 ml of a 1 M tetrahydrofuran solution) was added and the mixture was stirred at 0° for 1 hr. Dimethylcarbamoyl chloride (254 mg) was added to the mixture followed by gradual heating to reflux. The mixture was heated under reflux overnight and allowed to cool to ambient temperature. Water (100 ml) was added and the reaction mixture was evaporated. The residue was flash chromatographed on silica gel eluting first with 300 ml of hexane:ethyl acetate (2:1) then with 400 ml of hexane:ethyl acetate (1:1). The appropriate fractions were combined and evaporated. The residue was dried under vacuum to provide 231.7 mg (39.2%) product as an amorphous solid, mp 70°–80°.
ANALYSIS:
Calculated for $C_{26}H_{42}N_2O_7$: 63.12%C, 8.58%H, 5.66%N,
Found: 63.52%C, 8.62%H, 5.3%N

EXAMPLE 8

7β-(N,N-Diethylcarbamoyloxy)-8,13-epoxy-1α,6β,9α-trihydroxylabd-14-en-11-one-1,9-dimethylformamide acetal To a stirred solution of 1.0 g of 8,13-epoxy-1α,6β,7β,-9α-tetrahydrolabd-14-en-11-one-1,9-dimethylformamide acetal in 100 ml of dry tetrahydrofuran under nitrogen at 0° was added 2.83 ml of 1 M lithium bis(-trimethylsilyl)amide in tetrahydrofuran. The solution was stirred 20 min at 0°. To the solution was added 0.62 ml (0.66 g) of N,N-diethylcarbamoyl chloride. The solution was heated to ambient temperature, then to reflux and reflux was continued for 24 hr. The solution was allowed to cool to ambient temperature, poured into ice/water, diluted with ether, washed three times with water, once with saturated sodium chloride solution, and dried over anhydrous sodium sulfate. Filtration followed by evaporation of solvent provided an oil. The oil was dissolved in a minimum volume of 30% n-butyl acetate/hexane and flash chromatographed on silica gel, The column was eluted with 30% n-butyl acetate/hexane, 40% n-butyl acetate/hexane and 50% n-butyl acetate/hexane, The appropriate fraction was concentrated and the residue was crystallized from cyclohexane to provide 24 mg (18.9%) of product.
ANALYSIS:
Calculated for $C_{28}H_{46}N_2O_7$: 64.34%C, 8.87%H, 5.36%N,
Found: 64.50%C, 8.97%H, 5.25%N

EXAMPLE 9

8,13-Epoxy-7β-(N-hydroxylaminocarbonyloxy)-1α,6β,9α-trihydroxylabd-14-en-11-one-1,9-dimethylformamide acetal 8,13-Epoxy-1α,6β,7β,9α-tetrahydrolabd-14-en-11-one-1,9-dimethylformamide acetal (500 mg) was dissolved in 10 ml of dichloromethane together with 202.5 mg of 1,1′-carbonyldimidazole under nitrogen. The mixture was stirred at ambient temperature overnight. Hydroxylamine hydrochloride (1.6 g) was dissolved in 25 ml of methanol together with a single crystal of phenophthalein. Sufficient 25% sodium methoxide in methanol was added to turn the color of the solution pink. The sodium chloride was allowed to settle. An aliquot of 6 ml the hydroxylamine solution in methanol was added to the original solution and the mixture was stirred for 1 hr. The mixture was diluted with chloroform and extracted twice with water, once with 0.01 N hydrochloric acid and one with dilute sodium bicarbonate. The organic phase was dried over anhydrous sodium sulfate, filtered, and evaporated. The residue was flash chromatographed on silica gel in hexane:ethyl acetate (1:1), followed by hexane:ethyl acetate (1:2). The appropriate fractions were combined and evaporated and the residue was crystallized from hexane:ether to yield 200 mg (35.2%) of product, mp 119°–139°.
ANALYSIS:
Calculated for $C_{24}H_{38}N_2O_8$: 59.72%C, 7.95%H, 5.80%N,
Found: 59.46%C, 8.09%H, 5.41%N

EXAMPLE 10

8,13-Epoxy-7β-(N-methyl-N-hydroxylaminocarbonyloxy)-1α,6β,9α-trihydroxylabd-14-en-11-one-1,9-dimethylformamide acetal

8,13-Epoxy-1α,6β,7β,9α-tetrahydroxylabd-14-en-11-one-1,9-dimethylformamide acetal (500 mg) was dissolved in 10 ml of dichloromethane together with 202.5 mg of 1,1'-carbonyldiimidazole under nitrogen. The mixture was stirred at ambient temperature overnight. N-Methylhydroxylamine hydrochloride (3.6 g) was dissolved in 25 ml of methanol together with a single crystal of phenophthalein. Sufficient 25% sodium methoxide in methanol was added to change the color of the solution pink. The sodium chloride was allowed to settle out. An aliquot of 6 ml of the N-methylhydroxylamine in methanol solution was added to the original solution and the mixture was stirred for 1 hr. The mixture was diluted with chloroform and the solution was washed twice with water, once with 0.01 N hydrochloric acid and once with dilute sodium bicarbonate solution. The organic phase dried over anhydrous sodium sulfate, filtered and evaporated. The residue was flash chromatographed on silica gel in hexane:ethyl acetate (2:1) (1 l) and hexane/ethyl acetate (1:1). The appropriate fractions were combined and evaporated. The residue was crystallized from hexane:ether to yield 200 mg (34.2%) of product, mp 105°-119°.
ANALYSIS:
Calculated for $C_{25}H_{40}N_2O_5$: 60.46%C, 8.13%H, 5.64%N,
Found: 60.75%C, 8.54%H, 5.29%N

EXAMPLE 11

8,13-Epoxy-7β-(N-ethylaminocarbonyloxy)-1α,6β,9α-trihydroxylabd-14-en-11-one-1,9-dimethylformamide acetal

To a solution of 1.0 g of 8,13-epoxy-1α,6β,7β,9α-tetrahydrolabd-14-en-11-one-1,9-dimethylformamide acetal in 100 ml of dry tetrahydrofuran was added 0.237 ml of 1 M lithium bis(trimethylsilyl)amide in tetrahydrofuran. The solution was stirred for 0.5 hr at ambient temperature. To the solution was added 0.336 g of ethyl isocyanate. The solution was stored at reflux under nitrogen for 18 hr and allowed to cool to ambient temperature. The solution was diluted with ethyl acetate, poured into ice/water, extracted twice with ethyl acetate, washed with water, saturated sodium chloride solution and dried over anhydrous sodium sulfate. Filtration followed by evaporation of solvent provided an oil. The oil was dissolved in a minimum volume of 40% ethyl acetate; hexanes and flash chromatographed on silica gel using the same solvent system. Evaporation of solvent from the appropriate fractions provided 747 mg (63.5%) of product.
ANALYSIS:
Calculated for $C_{26}H_{42}N_2O_7$: 63.13%C, 8.56%H, 5.67%N,
Found: 62.90%C, 8.88%H, 5.47%N

EXAMPLE 12

8,13-Epoxy-7β-(N-methoxylaminocarbonyloxy)-1α,6β,9α-trihydroxylabd-14-en-11-one-1,9-dimethylformamide acetal

8,13-Epoxy-1α,6β,7β,9α-tetrahydroxylabd-14-en-11-one-1,9-dimethylformamide acetal (500 mg) was dissolved in 10 ml of dichloromethane together with 202.5 mg of 1,1'-carbonyldiimidazole, and the mixture was stirred under nitrogen at ambient temperature overnight. Methoxylamine hydrochloride (3.6 g) was dissolved in 25 ml of methanol together with a crystal of phenophthalein and sufficient 25% sodium methoxide in methanol was added to change the color of the solution to just pink. A 6.0 ml-aliquot of the methoxylamine solution was added to the original mixture and the resultant mixture was stirred under nitrogen at ambient temperature overnight. The reaction mixture was evaporated and the residue was flash chromatographed on silica gel in hexane: ethyl acetate (2:1). Evaporation of the appropriate fractions gave 144.3 mg (24.7%) of product, as an amorphous solid, mp 85°-92°.
ANALYSIS:
Calculated for $C_{25}H_{40}N_2O_8$: 60.46%C, 8.13%H, 5.64%N,
Found: 60.24%C, 8.42%H, 5.41%N

EXAMPLE 13

8,13-Epoxy-7β-(1-pyrrolidinocarbonyloxy)-1α,6β,9α-trihydroxylabd-14-en-11-one-1,9-dimethylformamide acetal

A solution of 500 mg of 8,13-epoxy-1α,6β,7β,9α-tetrahydroxylabd-14-en-11-one-1,9-dimethylformamide acetal in 50 ml of tetrahydrofuran containing 202.5 mg of 1,1'-carbonyldiimidazole was stirred at ambient temperature under nitrogen overnight. Pyrrolidine 417 μl (355 mg) was added and the mixture was stirred under nitrogen at ambient temperature for 3 hr and allowed to stand at ambient temperature for two and one-half days. The mixture was quenched with water and evaporated. The residue was dissolved in ether. The mixture was washed with water, dilute potassium carbonate solution, dried over anhydrous sodium sulfate and filtered. The filtrate was evaporated and the residue was flash chromatographed on silica gel in hexane:ethyl acetate (1:1). The appropriate fractions were combined and the residue was crystallized from hexane-ether to provide 30 mg (4.81%) of product, mp 218°-220°.

EXAMPLE 14

7β-(Aminocarbonyloxy)-8,13-epoxy-1α,6β,9α-trihydroxyabd-14-en-11-one

A solution of 128.4 mg of 7β-(aminocarbonyloxy)-8,13-epoxy-1α,6β,9α-trihydroxy-14-en-11-one-1,9-dimethylformamide acetal in 2 ml of 80% acetic acid and 2 ml of methanol was stirred at ambient temperature for 36 hrs. The mixture was evaporated and the residue was flash chromatographed on silica gel in hexane:ethyl acetate (1:1). The appropriate fractions were combined and evaporated. The residue was crystallized from hexane:ether to afford 50 mg (44.2%) of product, mp 124°-145°.
ANALYSIS:
Calculated for $C_{21}H_{33}NO_7$: 61.28%C, 8.10%H, 3.40%N,
Found: 61.09%C, 7.99%H, 3.35%N

EXAMPLE 15

8,13-Epoxy-7β-(N-methylaminocarbonyloxy)-1α,6β,9α-trihdroxylabd-14-en-11-one

A solution of 291.6 mg of 8,13-epoxy-7β-(N-methylaminocarbonyloxy)-1α,6β,9α-trihydroxylabd-14-en-11-one-1,9-dimethylformamide acetal in 6 ml of methanol:80% acetic acid (1:1) was stirred overnight under nitrogen at ambient temperature. The mixture was evaporated. The residue was suspended in ethyl acetate washed with aqueous sodium bicarbonate solution and evaporated. The residue was flash chromatographed on silica gel in hexane: ethyl acetate (1:1). The appropriate fractions were combined and evaporated. The residue was crystallized from hexane:ether to afford 67.4 mg (54.4%) of product, mp 133°–154°.
ANALYSIS:
Calculated for $C_{22}H_{35}NO_7$: 62.09%C, 8.31%H, 3.29%N,
Found: 61.35%C, 8.08%H, 3.17%N

EXAMPLE 16

8,13-Epoxy-7β-(4-morpholinocarbonyloxy)-1α,6β,9α-trihydroxylabd-14-en-11-one

A solution of 265.0 mg of 8,13-epoxy-7β-(4-morpholinocarbonyloxy)-1α,6β,9α-trihydroxylabd-14-en-11-one-1,9-dimethylformamide acetal in a mixture of 2 ml of 80% acetic acid and 2 ml of methanol was stirred at ambient temperature for 36 hr. The mixture was evaporated and the residue was flash chromatographed on silica gel in hexane:ethyl acetate (1:1). The appropriate fractions were combined and evaporated. The residue was crystallized from hexane:ether to provide 158.2 mg (65.8%) of product, mp 180°–188°.
ANALYSIS:
Calculated for $C_{25}H_{39}NO_8$: 62.34%C, 8.18%H, 2.91%N,
Found: 62.33%C, 8.11%H, 2.80%N

EXAMPLE 17

8,13-Epoxy-7β-(4-hydroxy-1-piperidinocarbonyloxy)-1α,6β,9α-trihydroxylabd-14-en-11-one A solution of 306.1 mg of 8,13-epoxy-7β-(4-hydroxy-1-piperidinocarbonyloxy)-1α,6β,9α-trihydroxylabd-14-en-11-one-1,9-dimethylformamide acetal in 2 ml of 80% acetic acid and 2 ml of methanol was stirred for 36 hr at ambient temperature. The solvent was evaporated and the residue was flash chromatographed on silica gel in hexane:ethyl acetate (1:2). The appropriate fractions were combined and evaporated. The residue was crystallized from hexane:ether to afford 185.1 mg (67.2%) of product, mp 145°–156°.
ANALYSIS:
Calculated for $C_{26}H_{41}NO_8$: 63.00%C, 8.35%H, 2.82%N,
Found: 62.71%C, 8.40%H, 2.79%N

EXAMPLE 18

8,13-Epoxy-7β-(1-pyrrolidinocarbonyloxy)-1α,6β,9α-trihydroxylabd-14-en-11-one solution of 300 mg 8,13-epoxy-7β-(1-pyrrolidinocarbonyloxy)-1α,6β,9α-trihydroxylabd-14-en-11-one-1,9-dimethylformamide acetal in 5 ml of 80% aqueous acetic acid and 5 ml of methanol was stirred at ambient temperature for 18 hr under nitrogen. The solvent was evaporated under vacuum. The residue was suspended in ethyl acetate and washed with saturated aqueous sodium bicarbonate solution. The ethyl acetate layer was evaporated and the residue was flash chromatographed on silica gel in hexane:ethyl acetate (2:1). The appropriate fractions were combined and evaporated. The residue was crystallized from hexane:ethyl acetate to afford 88.1 mg (31.6%) of product, mp 230°–233°.
ANALYSIS:
Calculated for $C_{25}H_{39}NO_7$: 64.48%C, 8.46%H, 3.01%N,
Found: 64.44%C, 8.48%H, 3.15%N

EXAMPLE 19

8,13-Epoxy-7β-(2-hydroxyethylaminocarbonyloxy)-1α,6β,9α-trihydroxylabd-14-en-11-one 8,13-Epoxy-7β-(2-hydroxyethylaminocarbonyloxy)-1α,6β,9α-trihydroxylabd-14-en-11-one-1,9 -dimethylformamide acetal (200 mg) was dissolved in a mixture of 2 ml of methanol and 2 ml of 80% acetic acid and stirred at ambient temperature under nitrogen for 3 days. The mixture was evaporated and the residue was flash chromatographed on silica gel in hexane:acetone (2:1). The appropriate fractions were combined, evaporated and crystallized from hexane:ethyl acetate to afford 92.4 mg (51.8%) of product, mp 116°–120°.
ANALYSIS:
Calculated for $C_{23}H_{37}NO_5$: 60.63%C, 8.20%H, 3.07%N,
Found: 60.47%C, 8.44%H, 3.14%N

EXAMPLE 20

7β-(N-2,3-Dihydroxypropylaminocarbonyloxy)-8,13-epoxy-1α,6β,9α-trihydroxylabd-14-en-11-one 7β-(N-2,3-Dihydroxypropylaminocarbonyloxy)-8,13-epoxy-1α,6β,9α-trihydroxylabd-14-en-11-one-1,9-dimethylformamide acetal (200 mg) was dissolved in a mixture of 2 ml of methanol and 2 ml of 80% acetic acid. The mixture was stirred under nitrogen at ambient temperature for 4 days. The mixture was evaporated and the residue flash chromatographed on silica gel in hexane:acetone (1:1). The appropriate fractions were combined and evaporated. The residue was crystallized from hexane:n-butyl acetate to afford 74.8 mg (41.6%) of product, mp 90°–105°.
ANALYSIS:
Calculated for $C_{24}H_{39}NO_9$: 59.35%C, 8.11%H, 2.88%N,
Found: 58.89%C, 8.29%H, 2.71%N

EXAMPLE 21

8,13-Epoxy-7β-(N-hydroxylaminocarbonyloxy)-1α,6β,9α-trihydroxylabd-14-en-11-one 8,13-Epoxy-1α,6β,7β,9α-trihydroxylabd-14-en-11-one-1,9-dimethylformamide acetal (1 g) was dissolved in 20 ml of dry dichloromethane together with 405 mg of 1,1'-carbonyldiimidazole, and the mixture was stirred under nitrogen overnight. Hydroxylamine (303.6 mg) generated from the hydrochloride in methanol by adding methanolic sodium methoxide was added to the original solution, and the resultant mixture was stirred overnight. The mixture was evaporated and the residue was flash chromatographed on silica gel in hexane:ethyl acetate (1:2). The fractions were combined and the residue was dissolved in 10 ml of methanol and 1 ml of 2 N hydrochloric acid, and the mixture was stirred at ambient temperature under nitrogen overnight. The mixture was evaporated. The residue was partitioned between saturated aqueous sodium bicarbonate and ethyl acetate. The ethyl acetate phase was dried over anhydrous sodium sulfate, filtered and evaporated. The residue was flash chromatographed on silica gel in hexane:ethyl acetate (1:1). The appropriate fractions were combined and evaporated. The residue was crystallized from hexane:ether to afford 152.0 mg (15.1%) of product, mp 209°–211°.
ANALYSIS:
Calculated for $C_{21}H_{33}NO_8$: 58.99%C, 7.80%H, 3.27%N,
Found: 58.85%C, 8.08%H, 3.24%N

EXAMPLE 22

8,13-Epoxy-7β-(N-methylhydroxylaminocarbonyloxy)-1α,6β,9α-trihydroxylabd-14-en-11-one 8,13-Epoxy-7β-(N-methylhydroxylaminocarbonyloxy)-1α,6β,9α-trihydroxylabd-14-en-11-one-1,9-dimethylformamide acetal (200 mg) was dissolved in 2 ml of 80% acetic acid and 2 ml of methanol. The mixture was stirred at ambient temperature under nitrogen for 36 hr and evaporated. The residue was dissolved in chloroform and extracted with saturated aqueous sodium bicarbonate solution. The organic phase was loaded onto a flash chromatography column of silica gel packed in hexane:ethyl acetate (2:1) and eluted with the same solvent mixture. The appropriate fractions were combined and evaporated. The residue was crystallized from hexane:ether to afford 90 mg of (50.6%) of product, mp 110°–145°.
ANALYSIS:
Calculated for $C_{22}H_{35}NO_8$: 59.84%C, 7.99%H, 3.17%N,
Found: 59.77%C, 7.94%H, 2.94%N

EXAMPLE 23

8,13-Epoxy-7β-(N-ethylaminocarbonyloxy)-1α,6β,9α-trihydroxylabd-14-en-11-one

A solution of 0.742 mg of 8,13-epoxy-7β-(N-ethylaminocarbonyloxy)-1α,6β,9α-trihydroxylabd-14-en-11-one-1,9-dimethylformamide acetal in 10 ml of methanol and 10 ml of 80% acetic acid was stirred at room temperature for 48 hr. The solution was diluted with ethyl acetate, washed three times with water and once with saturated sodium chloride solution. The solution was dried over anhydrous sodium sulfate, filtered and concentrated. The residue was dissolved in 1:1 n-butyl acetate/hexanes and flash chromatographed on silica gel. The initial fractions were combined and concentrated. The residue crystallized to provide 109 mg of product, mp 165°–167°. Subsequent fractions were combined and concentrated to provide an additional 163 mg of product. The total yield of product was 272 mg (41.3%).
ANALYSIS:
Calculated for $C_{23}H_{37}NO_7$: 62.85%C, 8.45%H, 3.15%N,
Found: 62.79%C, 8.47%H, 3.07%N

EXAMPLE 24

8,13-Epoxy-7-β(N-methoxylaminocarbonyloxy)-1α,6β,9α-trihydroxylabd-14-en-11-one 8,13-Epoxy-7β-(N-methoxylaminocarbonyloxy)-1α,6β,9α-trihydroxylabd-14-en-11-one-1,9-dimethylformamide acetal (121.5 mg) was dissolved in 2 ml of 80% acetic acid together with 2 ml of methanol. The mixture was stirred at ambient, temperature under nitrogen for 36 hr. The solvent was evaporated and the residue was flash chromatographed on silica gel eluting with hexane:ethyl acetate (65:35). The appropriate fractions were combined and evaporated. Crystallization of the residue from hexane:ether provided 40 mg (37%) of product, mp 100°–120°.
ANALYSIS:
Calculated for $C_{22}H_{35}NO_8$: 59.84%C, 7.99%H, 3.17%N,
Found: 60.03%C, 8.20%H, 2.94%N

EXAMPLE 25

8,13-Epoxy-7β-[N,N-bis-2-hydroxyethylaminocarbonyloxy)-1α,6β,9α-trihydroxylabd-14-en-11-one-1,9-dimethylformamide acetal To a stirred solution of 2.0 g of 8,13-epoxy-1α,6β,7β,-9α-tetrahydroxylabd-14-en-11-one-1,9-dimethylformamide acetal in 30 ml of dry ethyl acetate under nitrogen was added 0.814 g of 1,1'-carbonyldiimidazole. The solution was stirred at room temperature overnight. To the solution was added 2 ml of N,N-diethanolamine. The solution was stirred 24 hr at ambient temperature and flash chromatographed on silica gel. The column was eluted with 1/1 ethyl acetate/hexanes, 2/1 ethyl acetate/hexanes and ethyl acetate. The appropriate fractions were combined and concentrated to provide 0.34 g (17%) of product, as a foam, mp 97°–119°.
ANALYSIS:
Calculated for $C_{28}H_{46}N_2O_9$: 60.63%C, 8.36%H, 5.05%N,
Found: 60.90%C, 8.28%H, 4.97%N

EXAMPLE 26

8,13-Epoxy-6-(N-methylaminocarbonyloxy)-1α,7β,9α-trihydroxylabd-14-en-11-one

To a solution of 0.3 g of 8,13-epoxy-7β-(N-methylaminocarbonyloxy)-1α,6β,9α-trihydroxylabd-14-en-11-one in 10 ml of t-butanol and 1 ml of dry tetrahydrofuran was added 1.1 g of potassium t-butoxide. The solution was stirred for 1 hr at room temperature, poured into ice/water, washed twice with water, once with saturated sodium chloride solution and dried over anhydrous sodium sulfate. Filtration followed by evaporation of solvent provided an oil. The oil was dissolved in a minimum volume of 1:1 ethyl acetate:hexanes and chromatographed on silica gel eluting with 1:1 ethyl acetate:hexanes, followed by 3:2 ethyl acetate:hexanes. The appropriate fractions were combined and concentrated to an oil, which crystallized on standing to provide, after drying at 111° (1 mm), 180 mg (60%) of product, mp 242°–243°.
ANALYSIS:
Calculated for $C_{22}H_{35}NO_7$: 62.09%C, 8.29%H, 3.29%N,
Found: 62.29%C, 8.24H, 2.87%N

EXAMPLE 27

8,13-Epoxy-1α-(1-pyrrolidinocarbonyloxy)-6β,7β,9α-trihydroxylabd-14-en-11-one

A solution of 100 mg of 8,13-epoxy-1α,6β,7β,9α-tetrahydroxylabd-14-en-11-one was dissolved in 10 ml of dry tetrahydrofuran containing 44 mg of 1,1'-carbonyldiimidazole was stirred at ambient temperature under nitrogen for 1.5 hr. Pyrrolidine (83 μl, 71 mg) was added and the mixture was stirred overnight. The mixture was evaporated and the residue was suspended in ether, washed with dilute aqueous hydrochloric acid, water and dilute aqueous potassium carbonate. The ether phase was dried over anhydrous sodium sulfate, filtered and evaporated. The residue was flash chromatographed on silica gel in hexane:ethyl acetate (2:1). The appropriate fractions were combined and evaporated. The residue was recrystallized from cyclohexane:ethyl acetate to afford 40.0 mg (31.6%) of product, mp 207°–210°.
ANALYSIS:
Calculated for $C_{25}H_{39}NO_7$: 64.48%C, 8.46%H, 3.01%N,
Found: 64.62%C, 8.68%H, 3.12%N

EXAMPLE 28

8,13-Epoxy-7β-(N-propionylaminocarbonyloxy)-1α,6β,9α-trihydroxylabd-14-en-11-one 8,13-Epoxy-7β-(N-propionylaminocarbonyloxy)-1α,6β,9α-trihydroxylabd-14-en-11-one1,9-carbonate (1.6 g) was dissolved in 20 ml of pyridine and 20 ml of water. The solution was heated at reflux for 7 hrs and allowed to cool. The reaction mixture was diluted with 50 ml of methylene chloride and washed with 0.01 N hydrochloric acid and water. The organic layer was dried over anhydrous sodium sulfate and the solvent was removed under reduced pressure. The residue was chromatographed on silica gel. The column was eluted with hexane:ethyl acetate (3:2). The appropriate fractions were collected and the solvent was removed to give 660 mg (44%) of product, mp 115°–120°.
ANALYSIS:
Calculated for $C_{24}H_{37}NO_8$: 61.63%C, 7.99%H, 2.99%N,
Found: 61.18%C, 8.00%H, 2.65%N

EXAMPLE 29

8,13-Epoxy-7β-[N-(2-pyridylacetoxy)aminocarbonyloxy]-1α,6β,9α-trihydroxylabd-14-en-11-one hydrochloride To a stirred solution of 243 mg of 2-pyridylacetic acid hydrochloride in 25 ml of methylene chloride was added 0.2 ml of triethylamine. The mixture was stirred at room temperature for 0.5 hr and 227 mg of 1,1'-carbonyldiimidazole was added. After 45 mins a solution of 500 mg of 8,13-epoxy-7β-(hydroxyaminocarbonyloxy)-1α,6β,9α-trihydroxylabd-14-en-11-one in 5 ml of tetrahydrofuran and 25 ml of methylene chloride was added and the mixture was stirred overnight under a nitrogen atmosphere. The mixture was concentrated under reduced pressure and the residue was chromatographed on silica gel. The column was eluted with 1:1 hexane:ethyl acetate. The appropriate fractions were collected and the solvent was removed. The residue was dissolved in ether (50 ml) and ethereal hydrogen chloride was added. The precipitate was collected and dried to give 390 mg (57%) of product, mp 142° (dec).
ANALYSIS:
Calculated for $C_{28}H_{39}ClN_2O_9$: 57.66%C, 6.75%H, 4.80%N,
Found: 57.35%C, 7.12%H, 4.72%N

EXAMPLE 30

8,13-Epoxy-7β-[N-(4-methoxysuccinyl)oxyaminocarbonyloxy]-1α,6β,9α-trihydroxylabd-14-en-11-one To a stirred solution of 740 mg of mono-methylsuccinate in 100 ml of methylene chloride was added 910 mg of 1,1'-carbonyldiimidazole. The solution was stirred for 45 mins at room temperature under a nitrogen atmosphere. 8,13-Epoxy-7β-(hydroxyaminocarbonyloxy)-1α,6β,9α-trihydroxylabd-14-en-11-one (2.0 g) dissolved in 20 ml of tetrahydrofuran and 100 ml of methylene chloride was added and the resulting mixture was stirred 16 hrs. The mixture was concentrated and the residue was chromatographed on silica gel. The column was eluted with hexane:ethyl acetate (1:1). The appropriate fractions were collected and the solvent removed to give 1.6 g (63%) of product, mp 82°.
ANALYSIS:
Calculated for $C_{26}H_{39}NO_{11}$: 57.65%C, 7.27%H, 2.58%N,
Found: 57.62%C, 7.24%H, 2.49%N

EXAMPLE 31

8,13-Epoxy-7β-[N-(N',N'-dimethylcarbamoyloxy)aminocarbonyloxy]-1α,6β,9α-trihydroxylabd-14-en-11-one To a stirred solution of 1.0 g of 8,13-epoxy-7β-(hydroxyaminocarbonyloxy)-1α,6β,9α-trihydroxylabd-14-en-11-one in 90 ml of methylene chloride and 10 ml of tetrahydrofuran was added 283 mg of triethylamine followed by 308 mg of N,N-dimethylcarbamoyl chloride dissolved in 10 ml of methylene chloride. The mixture was stirred overnight at room temperature under a nitrogen atmosphere and then washed with 0.01 N hydrochloric acid, saturated sodium bicarbonate solution and water. The organic layer was separated, dried over anhydrous sodium sulfate and the solvent was removed. The residue was chromatographed on silica gel. The column was eluted with hexane:ethyl acetate (1:1). The appropriate fractions were collected and the solvent was removed to give 390 mg of product, mp 119°–120°.
ANALYSIS:
Calculated for $C_{24}H_{38}N_2O_9$: 57.80%C, 7.69%H, 5.62%N,
Found: 57.40%C, 7.70%H, 5.55%N

EXAMPLE 32

8,13-Epoxy-7β-(2-dimethylphosphinyl)ethylcarbonyloxy]aminocarbonyloxy)-1α,6β,9α-trihydroxylabd-14-en-11-one hydrate To a stirred solution of 316 mg of 2-(carboxyethyl)-dimethylphosphine oxide in 40 ml of methylene chloride was added 340 mg of 1,1'-carbonyldiimidazole. The solution was stirred at room temperature for 45 mins under a nitrogen atmosphere. 8,13-Epoxy-7β-(hydroxyaminocarbonyloxy)-1α,6β,9α-trihydroxylabd-14-en-11-one (750 mg) dissolved in 5 ml of tetrahydrofuran and 35 ml of methylene chloride was added and the mixture was stirred for 16 hrs. The reaction mixture was washed with water and saturated sodium bicarbonate solution. The organic portion was separated, dried over anhydrous sodium sulfate, filtered, and the solvent was removed to give 440 mg (45%), mp 201°–203° after crystallization from hexane:ethyl acetate.
ANALYSIS:
Calculated for $C_{26}H_{42}NO_{10}P$: 54.05%C, 7.69%H, 2.43%N,
Found: 54.32%C, 7.37%H, 2.44%N

EXAMPLE 33

8,13-Epoxy-7β-[N-(tetrahydro-2-furoyloxy)aminocarbonyloxy]-1α,6β,9α-trihydroxylabd-14-en-11-one To a stirred solution of 650 mg of tetrahydro-2-furoic acid dissolved in 75 ml of methylene chloride was added 910 mg of 1,1'-carbonyldiimidazole. The mixture was allowed to stir at room temperature under an atmosphere of nitrogen for 0.5 hr. 8,13-Epoxy-7β-(hydroxyaminocarbonyloxy)-1α,6β,9α-trihydroxylabd-14-en-11-one (2.0 g) was dissolved in 75 ml of methylene chloride and 5 ml of tetrahydrofuran and was added to the reaction mixture. The reaction mixture was stirred under nitrogen for 3 hrs. The solution was concentrated to a final volume of 15 ml and flash chromatographed on silica gel. The column was elated with 1:1 hexane:ethyl acetate. The appropriate fractions were combined and the solvent was removed. Recrystallization frown hexane/ethyl acetate gave 380 mg (16%) of product, mp 200°–203°.
ANALYSIS:
Calculated for $C_{26}H_{39}NO_{10}$: 59.41%C, 7.49%H, 2.66%N,
Found: 59.41%C, 7.43%H, 2.68%N

EXAMPLE 34

8,13-Epoxy-7β-[N-2,2-(dimethylpropionyloxy)aminocarbonyloxy]-1α,6β,9α-trihydroxylabd-14-en-11-one Pivalic acid (143 mg) dissolved in 10 ml of dichloromethane was stirred with 228 mg of 1,1'-carbonyldiimidazole dissolved in 40 ml of dichloromethane under nitrogen for 20 min at ambient temperature. 8,13-Epoxy-7β-(N-hydroxyaminocarbonyl)-1α,6β,9α-trihydroxylabd-14-en-11-one (500 mg) dissolved in 55 ml of 10:1 tetrahydrofuran in dichloromethane was added, and the resultant mixture was stirred overnight. The mixture was evaporated to a final volume of 20 ml and flash chromatographed on silica gel in 3:1 hexane:ethyl acetate. The appropriate fractions were combined and evaporated. The residue was crystallized from hexane:ether to give 238 mg (38.8%) of product, mp 105°–108°.
ANALYSIS:
Calculated for $C_{26}H_{41}NO_9$: 61.03%C, 8.09%H, 2.74%N,
Found: 61.47%C, 8.39%H, 2.91%N

EXAMPLE 35

8,13-Epoxy-7β-(N-propylaminocarbonyloxy)-1α,6β,9β-trihydroxylabd-14-en-11-one 8,13-Epoxy-7β-(N-propylaminocarbonyloxy)-1α,6β,9α-labd-14-en-11-one-1,9-dimethylformamide acetal (657.4 mg) was dissolved in 21 ml of methanol and 7 ml of water. The mixture was stirred under nitrogen at 60° for 5 days. The mixture was evaporated. The residue was partitioned between ethyl acetate and 1 N hydrochloric acid. The organic phase was separated and washed with 1 N hydrochloric acid, water, saturated sodium bicarbonate solution and saturated sodium chloride solution. The ethyl acetate solution was dried over anhydrous sodium sulfate, filtered and evaporated. The residue was dissolved in methanol and the solution was poured into water with vigorous stirring. The precipitate was collected and vacuum dried at 100° to provide 337 mg (57.6%) of product, mp 120°–123°.
ANALYSIS:
Calculated for $C_{24}H_{39}NO_7$: 63.54%C, 8.68%H, 3.09%N,
Found: 63.45%C, 8.65%H, 2.97%N

EXAMPLE 36

8,13-Epoxy-7β-(N-acetoxyaminocarbonyloxy)-1α,6β,9α-trihydroxylabd-14-en-11-one

To a stirred solution of 250 mg of acetic acid in 50 ml of methylene chloride was added 680 mg of 1,1'-carbonyldiimidazole. The mixture was stirred for 45 mins under a nitrogen atmosphere. 8,13-Epoxy-7β-(N-hydroxyaminocarbonyloxy)-1α,6β,9α-trihydroxylabd-14-en-11-one (1.5 g) dissolved in 50 ml of methylene chloride and 10 ml of tetrahydrofuran was added, and the reaction mixture was stirred under a nitrogen atmosphere for 48 hrs. The solution was concentrated to a final volume of 15 ml and the residue was flash chromatographed on silica gel. The column was eluted with 1:1 hexane:ethyl acetate. The appropriate fractions were combined, the solvent was removed, and the residue was crystallized from hexane:ethyl acetate to give 680 mg (42%) of product, 98°–103°.
ANALYSIS:
Calculated for $C_{23}H_{35}NO_9$: 58.82%C, 7.53%H, 2.98%N,
Found: 58.59%C, 7.52%H, 3.33%N

EXAMPLE 37

8,13-Epoxy-7β-(N-propionyloxyaminocarbonyloxy)-1α,6β,9α-trihydroxylabd-14-en-11-one To a stirred solution of 250 mg of propionic acid in 50 ml of methylene chloride was added 540 mg of 1,1'-carbonyldiimidazole. The mixture was stirred under a nitrogen atmosphere for 1 hr at room temperature. A solution of 1.2 g of 8,13-epoxy-7β-(N-hydroxyaminocarbonyloxy)-1α,6β,9α-trihydroxylabd-14-en-11-one in 50 ml of methylene chloride and 1 ml of tetrahydrofuran was added and the reaction mixture was stirred for 48 hrs. The solution was concentrated and the residue was flash chromatographed on silica gel. The column was eluted with 1:1 hexane:ethyl acetate. The appropriate fractions were combined and the solvent was removed. The residue was crystallized from hexane:ether to give 710 mg (53%) of product, mp 110°–114°.
ANALYSIS:
Calculated for $C_{24}H_{37}NO_9$: 59.61%C, 7.71%H, 2.90%N,
Found: 59.24%C, 7.67%H, 3.10%N

EXAMPLE 38

8,13-Epoxy-7β-[N-(2-methylpropionyloxy)aminocarbonyloxy]-1α,6β,9α-trihydroxylabd-14-en-11-one To a stirred solution of 300 mg of isobutyric acid in 50 ml of methylene chloride was added 540 mg of 1,1'-carbonyldiimidazole and the resulting mixture was stirred at room temperature under a nitrogen atmosphere for 1 hr. 8,13-Epoxy-7β-(N-hydroxyaminocarbonyloxy)-1α,6β,9α-trihydroxylabd-14-en-11-one (1.2 g) dissolved in 10 ml of tetrahydrofuran and 50 ml of methylene chloride was added dropwise, and the mixture was allowed to stir overnight. The solution was concentrated and the residue was chromatographed on silica gel. The column was eluted with hexane:ethyl acetate (2:1). The appropriate fractions were collected and the solvent was removed under reduced pressure to give 1.02 g (71%) of product, mp 100°–110°.
ANALYSIS:
Calculated for $C_{25}H_{31}NO_9$: 60.33%C, 7.91%H, 2.81%N,
Found: 60.01%C, 8.20%H, 3.10%N

EXAMPLE 39

8,13-Epoxy-7β-[N-(1-methylpiperidin-4-yl-carbonyloxy)aminocarbonyloxy]-1α,6β,9α-trihydroxylabd-14-en-11-one hydrochloride hydrate To a stirred solution of 503 mg 1-methylpiperidin-4-yl-carboxylic acid hydrochloride in 50 ml of methylene chloride was added 282 mg of triethylamine. The mixture was stirred at 0° for 15 mins and then 455 mg of 1,1'-carbonyldiimidazole was added. The reaction mixture was stirred for 45 mins at room temperature under a nitrogen atmosphere. 8,13-Epoxy-7β-(N-hydroxyaminocarbonyloxy)-1α,6β,9αlabd-14-en-11-one (1.0g) dissolved in 5 ml of tetrahydrofuran and 50 ml of methylene chloride was added and the mixture was stirred overnight at room temperature. The reaction mixture was washed with water, 0.01 N hydrochloric acid and saturated sodium bicarbonate solution, dried over anhydrous sodium sulfate, filtered, and the solvent was removed under reduced pressure. A sample (600 mg) of the residue (1.2 g) was dissolved in ether and ethereal hydrogen chloride was added until the pH remained slightly acidic. The product was collected and dried under vacuum to give 370 mg (56%) of product, mp 168° (dec).

ANALYSIS:
Calculated for $C_{28}H_{47}ClN_2O_{10}$: 55.38%C, 7.82%H, 4.61%N,
Found: 55.19%C, 7.44%H, 4.81%N

EXAMPLE 40

8,13-Epoxy-7β-N-(3-hydroxypropyl)aminocarbonyloxy]-1α,6β,9α-trihydroxylabd-11-en-14-one A stirred solution of 1.8 g 8,13-epoxy-7β-[N-(3-hydroxypropyl)aminocarbonyloxy]-1α,6β,9α-trihydroxylabd-14-en-11-one-1,9-dimethylformamide acetal in 50 ml of methanol and 16 ml of water was heated at 60° for 72 hrs. The reaction mixture was allowed to cool to room temperature, water (20 ml) was added and the mixture was extracted with methylene chloride. The methylene chloride layer was dried over anhydrous sodium sulfate, filtered, and the solvent was removed. The residue was chromatographed on silica gel. The column was eluted with hexane:ethyl acetate:methanol (1:1:0.1). The appropriate fractions were collected and the solvent was removed to give 1.3 g (81%) of product, mp 188°.

ANALYSIS:
Calculated for $C_{24}H_{39}NO_8$: 61.37%C, 8.39%H, 2.98%N,
Found: 61.39%C, 8.43%H, 2.94%N

EXAMPLE 41

8,13-Epoxy-7β-[(N-propionyloxy-N-methyl)aminocarbonyloxy]-1α,6β,9α-trihydroxylabd-14-en-11-one To a stirred solution of 164 mg of propionic acid in 50 ml of methylene chloride was added 360 mg of 1,1'-carbonyldiimidazole. The mixture was stirred at room temperature under a nitrogen atmosphere for 45 mins. A solution of 1.0 g of 8,13-epoxy-7β-(N-methyl-N-hydroxy)aminocarbonyloxy)-1α,6β,9α-trihydroxylabd-14-en-11-one in 10 ml of tetrahydrofuran and 50 ml of methylene chloride was added and the mixture was stirred for 16 hrs. The reaction mixture was concentrated and the residue was chromatographed on silica gel. The column was eluted with hexane:ethyl acetate (3:2). The appropriate fractions were collected and the solvent was removed under reduced pressure to give 660 mg (59.8%) of product, mp 194°.

ANALYSIS:
Calculated for $C_{25}H_{39}NO_9$: 60.33%C, 7.91%H, 2.81%N,
Found: 60.46%C, 7.87%H, 2.68%N

EXAMPLE 42

8,13-Epoxy-7β-[N-(2-oxopropyl)aminocarbonyloxy]-1α,6β,9α-trihydroxylabd-14-en-11-one 8,13-Epoxy-7β-[(N-2-oxopropyl)aminocarbonyloxy]-1α,6β,9α-trihydroxylabd-14-en-11-one-1,9-dimethylformamide acetal (1.7 g) was dissolved in 50 ml of methanol and 20 ml of water. The mixture was heated in an oil bath at 60° for 72 hrs. The reaction mixture was cooled to room temperature and extracted with methylene chloride. The methylene chloride extracts were dried over anhydrous sodium sulfate and the solvent was removed. The residue was chromatographed on silica gel. The column was eluted with 1:1 hexane:ethyl acetate. The appropriate fractions were collected and the solvent was removed to give 1.04 g (69.7%) of product, mp 192°.

ANALYSIS:
Calculated for $C_{24}H_{37}NO_8$: 61.64%C, 7.99%H, 2.99%N,
Found: 61.70%C, 7.96%H, 2.87%N

EXAMPLE 43

7β-(N-Cyclopropylcarbonyloxyaminocarbonyloxy)-1α,6β,9α-trihydroxylabd-14-en-11-one To a stirred solution of 241 mg of cyclopropanecarboxylic acid in 50 ml of methylene chloride was added 454 mg of 1,1'-carbonyldiimidazole. The mixture was stirred for 1 hr, and 1.0 g of 8,13-epoxy-7β-(hydroxylaminocarbonyloxy)-1α,6β,9α-trihydroxylabd-14-en-11-one dissolved in 50 ml of methylene chloride and 10 ml of tetrahydrofuran was added. The reaction mixture was stirred for 16 hrs at room temperature under a nitrogen atmosphere. The mixture was concentrated and the residue was chromatographed on silica gel. The column was eluted with hexane:ethyl acetate (2:1). The appropriate fractions were collected and the solvent removed to give 870 mg of product, mp 198°.

ANALYSIS:
Calculated for $C_{25}H_{37}NO_9$: 60.58%C, 7.54%H, 2.33%N,
Found: 60.57%C, 7.56%H, 2.77%N

EXAMPLE 44

8,13-Epoxy7β-[N-(2-methoxy-2-methylpropionyloxy)aminocarbonyloxy)-1α,6β,9α-trihydroxylabd-14-en-11-one To a stirred solution of 330 mg of 2-methoxyisobutyric acid and 50 ml of methylene chloride was added 454 mg of 1,1'-carbonyldiimidazole. The mixture was stirred at room temperature for 1 hr and then 1.0 g 8,13-epoxy-7β-(hydroxylaminocarbonyloxy)-1α,6β,9α-trihydroxylabd-14-en-11-one dissolved in 50 ml of methylene chloride and 10 ml tetrahydrofuran was added. The mixture was stirred overnight at room temperature under a nitrogen atmosphere and was concentrated under reduced pressure. The residue was chromatographed on silica gel. The column was eluted with hexane:ethyl acetate (1:1). The appropriate fractions were collected and the solvent was removed. The residue was crystallized from hexane:ethyl acetate to give 1.01 g (83%) of product, mp 17820.
ANALYSIS:
Calculated for $C_{26}H_{41}NO_{10}$: 59.17%C, 7.84%H, 2.65%N,
Found: 59.15%C, 7.80%H, 2.5%N

EXAMPLE 45

7β-[N-(3,3-Dimethylacryloyloxy)aminocarbonyloxy]-8,13-epoxy-1α,6β,9α-trihydroxylabd-14-en-11-one To a stirred suspension of 1.0 g of 8,13-epoxy-7β-(hydroxyaminocarbonyloxy)-1α,6β,9α-trihydroxylabd-14-en-11-one and 280 mg of 3,3-dimethylacrylic acid in 100 ml of methylene chloride was added 530 mg of 1-(3-dimethylaminopropyl)-3-ethylcarbodiimide hydrochloride followed by 340 mg of 4-dimethylaminopyridine. The mixture was stirred for 1 hr under an atmosphere of nitrogen and then washed with 0.01 N hydrochloric acid, saturated, sodium bicarbonate solution and water. The organic layer was separated, dried over anhydrous sodium sulfate and filtered. The solvent was removed under reduced pressure and the residue was chromatographed on silica gel. The column was eluted with hexane:ethyl acetate (3:2). The appropriate fractions were collected and the solvent was removed to give 0.52 g of product, mp 105°–110°.
ANALYSIS:
Calculated for $C_{26}H_{39}NO_9$: 61.27%C, 7.73%H, 2.75%N,
Found: 60.95%C, 7.71%H, 2.66%N

EXAMPLE 46

8,13-Epoxy-7β-[N-(3,-methoxyacetoxy)aminocarbonyloxy]-1α,6β,9α-trihydroxylabd-14-en-11-one To a stirred suspension of 1.0 g of 8,13-epoxy-7β(hydroxyaminocarbonyloxy)-1α,6β,9α-trihydroxylabd-14-en-11-one and 252 mg of methoxyacetic acid in 100 ml of methylene chloride was added 530 mg of 1-(3'-dimethylpropyl)-3-ethylcarbodiimide hydrochloride and 340 mg of 4-dimethylaminopyridine. The mixture was stirred at room temperature under an atmosphere of nitrogen for 1 hr. The reaction mixture was washed with water, 0.01 N hydrochloric acid and saturated sodium bicarbonate solution. The methylene chloride layer was separated, dried over anhydrous sodium sulfate, and the solvent was removed. The residue was crystallized from hexane:ethyl acetate to give 0.5 g (43%) of product, mp 191°.
ANALYSIS:
Calculated for $C_{24}H_{37}NO_{10}$: 57.69%C, 7.47%H, 2.80%N,
Found: 57.59%C, 7.58%H, 2.89%N

EXAMPLE 47

6,β-(Aminocarbonyloxy)-8,13-epoxy)-1α,7β,9α-trihydroxylabd-14-en-11-one

To a stirred solution of 524 mg of 7β-(aminocarbonyloxy)-8,13-epoxy-1α,6β,9α-trihydroxylabd-14-en-11-one in 20 ml of t-butanol under nitrogen was added 1.9 g of potassium t-butoxide. The solution was stirred for 1 hr at room temperature under nitrogen, poured into ice water:ethyl acetate and extracted twice with ethyl acetate. The combined organic layers were washed with water, saturated sodium chloride solution, dried over anhydrous sodium sulfate, and filtered. The filtrate was evaporated. The residue was purified by flash chromatography on silica gel eluting with 60% ethyl acetate:hexanes followed by 75% ethyl acetate:hexanes. The appropriate fractions were combined to provide, after crystallization from ethyl acetate:hexanes, 0.076 g (14.6%) of product, mp 225°–227.
ANALYSIS:
Calculated for $C_{21}H_{33}NO_7$: 61.29%C, 8.08%H, 3.40%N,
Found: 61.25%C, 8.13%H, 3.14%N

EXAMPLE 48

7β-N-(1-Oxo-3-butenyl)oxyaminocarbonyloxy]-8,13-epoxy-1α,6β,9α-trihydroxylabd-14-en-11-one To a stirred solution of 1.81 mg of 3-butenoic acid in 35 ml of methylene chloride was added 340 mg of 1,1'-carbonyldiimidazole. The mixture was stirred at room temperature under a nitrogen atmosphere for 45 mins and then a solution of 750 mg of 8,13-epoxy-7β-(hydroxylaminocarbonyloxy)-1α,6β,9α-trihydroxylabd-14-en-11-one in 40 ml of methylene chloride and 5 ml of tetrahydrofuran was added. The mixture was stirred overnight at room temperature under an atmosphere of nitrogen and then concentrated at reduced pressure. The residue was chromatographed on silica gel. The column was eluted with hexane:ethyl acetate (1:1). The appropriate fractions were collected and the solvent removed to give 245 mg (28%) of product, mp 93°–98°.
ANALYSIS:
Calculated for $C_{25}H_{37}NO_9$: 60.57%C, 7.57%H, 2.82%N,
Found: 60.87%C, 7.52%H, 2.60%N

EXAMPLE 49

7β-(N-Acryloxyaminocarbonyloxy)-8,11-epoxy-1α,6β,9α-trihydroxylabd-14-en-11-one

To a stirred solution of 200 mg of acrylic acid in 50 ml of methylene chloride at 0° was added 283 mg of triethylamine followed by 332 mg of trimethylacetyl chloride. The mixture was stirred at 0° under a nitrogen atmosphere for 45 mins. A solution of 1.0 g of 8,13-epoxy-7β-(hydroxylaminocarbonyloxy)-1α,6β,9α-trihydroxylabd-14-en-11-one and 34 mg of 4-dimethylaminopyridine in 50 ml of methylene chloride and 10 ml of tetrahydrofuran was added to the cold reaction mixture. The mixture was stirred at 0° for 0.5 hr. The reaction mixture was washed with water, 0.01 N hydrochloric acid and saturated sodium bicarbonate solution, dried over anhydrous sodium sulfate and filtered. The solvent was removed and the residue was chromatographed on silica gel. The column was eluted with hexane:ethyl acetate (1:1). The appropriate fractions were collected and the solvent removed to give 0.4 g (36%) of product, mp 115°–120°.
ANALYSIS:
Calculated for $C_{24}H_{35}NO_9$: 59.85%C, 7.34%H, 2.91%N,
Found: 59.63%C, 7.34%H, 2.72%N

EXAMPLE 50

8,13-Epoxy-6β-(1-pyrrollidinocarbonyloxy)-1α,7β,9α-trihydroxylabd-14-en-11-one 8,13-Epoxy-6β-(1-pyrrolidinocarbonyloxy)-1α,6β,9α-trihydroxylabd-14-en-11-one-1,9-dimethylformamide acetal (2.7 g), was dissolved in 70 ml of methanol and 20 ml of water. The mixture was stirred at 55° for 74 hrs. After cooling to room temperature, the reaction mixture was diluted with saturated sodium chloride solution and extracted with ethyl acetate. The ethyl acetate extracts were dried over anhydrous sodium sulfate and the solvent was removed under reduced pressure. The residue was chromatographed on silica gel. The column was eluted with hexane:acetone (2:1). The appropriate fractions were collected and the solvent was removed to give 1.2 g (50%) of product, mp 135°–140°.
ANALYSIS:
Calculated for $C_{25}H_{39}NO_7$: 64.48%C, 8.46%H, 3.01%N,
Found: 64.35%C, 8.49%H, 2.90%N

EXAMPLE 51

8,13-Epoxy-6β-[N-(2-hydroxyethyl)aminocarbonyloxy]-1α,7β,9α-trihydroxylabd-14-en-11-one 8,13-Epoxy-6β-[N-(2-hydroxyethyl)aminocarbonyloxy]-1α,7β,9α-trihydroxylabd-14-en-11-one-1,9-dimethylformamide acetal (1.1 g) was dissolved in 30 ml of methanol and 10 ml of water. The mixture was stirred at 55° for 72 hrs. After cooling to room temperature, the reaction mixture was diluted with saturated sodium chloride solution and extracted with ethyl acetate. The ethyl acetate extracts were dried over anhydrous sodium sulfate, filtered, and the solvent was removed under reduced pressure. The residue was chromatographed on silica gel. The column was eluted with hexane:acetone (1:1). The appropriate fractions were collected and the solvent was removed to give 0.63 mg (62%) of product as an amorphous solid, mp 125°–140°.
ANALYSIS:
Calculated for $C_{23}H_{37}NO_8$: 60.63%C, 8.20%H, 3.08%N,
Found: 60.44%C, 8.08%H, 2.94%N

EXAMPLE 52

6β-(N,N-Dimethylaminocarbonyloxy)-1α,7β,9α-trihydroxylabd-14-en-11-one

To a stirred solution of 1.5 g of 8,13-epoxy-7β-(N,N-dimethylaminocarbonyloxy)-1α,6β,9α-trihydroxylabd-14-en-11-one in 50 ml of t-butanol and 5 ml of tetrahydrofuran at 0° was added 5.3 g of potassium t-butoxide. The mixture was stirred under nitrogen atmosphere at 0° for 20 mins. The ice/water bath was removed and the reaction mixture was stirred an additional 4 hrs at room temperature. The reaction mixture was poured into an ice/water mixture and extracted with ethyl acetate. The ethyl acetate extracts were washed with water, saturated sodium chloride solution, dried over anhydrous sodium sulfate, and filtered. The filtrate was evaporated. The residue was flash chromatographed on silica gel. The column was eluted with 1:1 ethyl acetate:hexane followed by 2:1 ethyl acetate:hexane. The appropriate fractions were combined, the solvent was removed and the residue was crystallized from hexane:ethyl acetate to give 870 mg (51.3%) of product, mp 212°–215°.
ANALYSIS:
Calculated for $C_{23}H_{37}NO_7$: 62.84%C, 8.50%H, 3.18%N,
Found: 62.53%C, 8.35%H, 3.31%N

EXAMPLE 53

8,13-Epoxy-7β-(N-ethoxyaminocarbonyloxy)-1α,6β,9α-trihydroxylabd-14-en-11-one 8,13-Epoxy-7β-(N-ethoxyaminocarbonyloxy)-1α,6β,9α-trihydroxylabd-14-en-11-one-1,9-dimethylformamide acetal (2.0 g) was dissolved in 50 ml of methanol and 16 ml of distilled water. The solution was heated at 60° for 72 hrs. After cooling to room temperature, the mixture was diluted with 20 ml saturated sodium chloride solution and extracted with ethyl acetate. The ethyl acetate extracts were dried over anhydrous sodium sulfate, filtered, and the solvent was removed. The residue was chromatographed on silica gel. The appropriate fractions were combined and the solvent was removed. Crystallization from hexane:ether gave 900 mg (50.6%) of product, mp 105°.
ANALYSIS:
Calculated for $C_{23}H_{37}NO_8$: 60.63%C, 8.20%H, 3.08%N,
Found: 60.79%C, 8.63%H, 3.33%N

EXAMPLE 54

8,13-Epoxy-7β-(N-propylaminocarbonyloxy)-1α,6β,9α-14-en-11-one-dimethylformamide acetal 8,13-Epoxy-1α,6β,7β,9α-tetrahydroxylabd-14-en-11-one-1,9-dimethylformamide acetal (1.0 g) was dissolved in 100 ml of tetrahydrofuran and 230 ul of a 1 M solution of lithium bis(trimethylsilyl)amide at ambient temperature under nitrogen. The mixture was allowed to equilibrate for 15 min. Propyl isocyanate (435 ul, 391.5 mg) was added after which the mixture was stirred at 50° for 1 hr. The reaction mixture was quenched with 1 ml of water and evaporated. The residue was partitioned between ether and saturated aqueous sodium bicarbonate solution. The ether layer was evaporated. The residue was flash chromatographed on silica gel in hexane:ethyl acetate (3:1). The appropriate fractions were combined and evaporated. The residue was dissolved in ether and evaporated several times to provide a foam which was then vacuum dried at 60° to give 694 mg (59.4%) of product, mp 83°–90°.
ANALYSIS:
Calculated for $C_{27}H_{44}N_2O_7$: 63.74%C, 8.74%H, 5.50%N,
Found: 63.63%C, 8.68%H, 5.35%N

EXAMPLE 55

8,13-Epoxy-7β-(N-ethoxyaminocarbonyloxy)-1α,6β,9α-trihydroxylabd-14-en-11-one-1,9-dimethylformamide acetal To a stirred solution of 5.0 g of 8,13-epoxy-,1α,6β,7β,9α-tetrahydroxylabd-14-en-11-one-1,9-dimethylformamide acetal in 100 ml of methylene chloride was added 2.3 g of 1,1′-carbonyldiimidazole. The solution was stirred at room temperature overnight under a nitrogen atmosphere. A solution of O-ethylhydroxylamine was prepared by dissolving 2.9 g of O-ethyl hydroxylamine hydrochloride in 33 ml of methanol and phenolthalien as an indicator. A 25% sodium methoxide in methanol solution (7.0 ml) was added until the color remained light pink. The O-ethylhydroxylamine solution was added to the reaction mixture. After four days, the mixture was diluted with 100 ml methylene chloride washed with 0.01 N hydrochloric acid, saturated sodium bicarbonate solution and water. The organic layer was separated, dried over sodium sulfate, filtered, and the solvents were removed. The residue was chromatographed on silica gel, eluting with hexane:ethyl acetate (1:1). The appropriate fractions were collected and the solvent was removed to give 3.0 g (50%) of product, as a foam, mp 90°–95°.
ANALYSIS:
Calculated for $C_{26}H_{42}N_2O_8$: 61.14%C, 8.31%H, 5.48%N, Found: 60.87%C, 8.20%H, 5.57%N

EXAMPLE 56

8,13-Epoxy-6β-[N-(2-hydroxyethyl)aminocarbonyloxy]-1α,7β9α-trihydroxylabd-14-en-11-one-1,9-dimethylformamide acetal To a stirred solution of 300 mg of 8,13-epoxy-1α,6β,7β,9α-tetrahydroxylabd-14-en-11-one-1,9-dimethylformamide acetal in 6 ml of methylene chloride was added 140 mg of 1,1'-carbonyldiimidazole followed by 0.2 ml of triethylamine. The mixture was stirred 24 hrs at room temperature under an atmosphere of nitrogen. Ethanolamine (200 mg) was added and the mixture was stirred an additional 16 hrs. The mixture was diluted with 10 ml of methylene chloride and washed with 0.01 N hydrochloric acid until the washings were neutral. The organic portion was dried over anhydrous sodium sulfate and the solvent was removed. The residue was chromatographed on silica gel. The column was eluted with hexane:ethyl acetate:methanol (1:1:0.1). The appropriate fractions were collected and the solvent was removed to give 240 mg (66%) of product, mp 116°–120°.

ANALYSIS:
Calculated for $C_{26}H_{42}N_2O_8$: 61.14%C, 8.31%H, 5.48%N,
Found: 60.91%C, 8.35%H, 5.33%N

EXAMPLE 57

8,13-Epoxy-6β-(1-pyrrolidinocarbonyloxy)-1α,7β,9α-trihydroxylabd-14-en-11-one-1,9-dimethylformamide acetal 8,13-Epoxy-1α,6β,7β,9α-trihydroxylabd-14-en-11-one-1,9-dimethylformamide acetal (3.0 g) was dissolved in 60 ml of methylene chloride and 1.38 g of 1,1'-carbonyldiimidazole was added followed by 1.65 g of triethylamine. After stirring for 24 hrs at room temperature, pyrrolidine (2.5 g) was added and the mixture was stirred for 48 hrs. The reaction mixture was diluted with 50 ml of methylene chloride and extracted repeatedly with 0.01 N hydrochloric acid until the washing were acidic. The organic layer was dried over anhydrous sodium sulfate, filtered and the solvent was removed. The residue was chromatographed on silica gel. The column was eluted with 2:1 hexane:acetone. The appropriate fractions were collected and the solvent was removed to give 3.06 g (82%) of product as an amorphous solid.

ANALYSIS:
Calculated for $C_{28}H_{44}N_2O_7$: 64.58%C, 8.53%H, 5.38%N,
Found: 64.22%C, 8.35%H, 5.34%N

EXAMPLE 58

8,13-Epoxy-7β-(N-methyl-N-propionylaminocarbonyloxy)-1α,6β,9α-trihydroxylabd-14-en-11-one-1,9-dimethylformamide acetal To a stirred solution of 4.0 g of 8,13-epoxy-1α,6β,7β,9α-tetrahydroxylabd-14-en-11-one-1,9-dimethylformamide acetal in 80 ml of tetrahydrofuran at 0° was added 11.2 ml of a 1 M solution in THF of lithium bis(trimethylsilyl)amide. The mixture was stirred at 0° for 45 mins and 2.95 g of N-methyl-N-propionylcarbamoyl chloride was added. The reaction mixture was slowly warmed to reflux temperature and was refluxed for 16 hrs. After cooling to room temperature, the mixture was diluted with 200 ml of methylene chloride and washed with water. The organic phase was dried over anhydrous sodium sulfate, filtered, and the solvent was removed. The residue was chromatographed on silica gel. The column was eluted with 1:1 hexane:ethyl acetate. The appropriate fractions were collected and the solvent was removed to give 3.02 g (59.9%) of product as an oil.

ANALYSIS:
Calculated for $C_{28}H_{44}N_2O_8$: 62.65%C, 8.28%H, 5.22%N,
Found: 62.44%C, 8.65%H, 5.15%N

EXAMPLE 59

8,13-Epoxy-7β-[N-(3-hydroxypropyl)aminocarbonyloxy]-1α,6β,9α-labd-14-en-11-one-1,9-dimethylformamide acetal To a stirred solution of 3.0 g of 8,13-epoxy-1α,6β,7β,9α-tetrahydroxylabd-14-en-11-one-1,9-dimethylformamide acetal in 60 ml of methylene chloride was added 1.38 g of 1,1'-carbonyldiimidazole. The mixture was stirred under a nitrogen atmosphere at room temperature for 16 hrs. 3-Aminopropanol (2.64 g) dissolved in 10 ml of methylene chloride was added to the reaction mixture, and the mixture was stirred for 18 hrs at room temperature. The reaction mixture was diluted with 50 ml of methylene chloride and washed with 0.01 N hydrochloric acid until the washings remained acidic. The methylene chloride layer was dried over anhydrous sodium sulfate, filtered, and the filtrate was concentrated. The residue was chromatographed on silica gel. The column was eluted with hexane:ethyl acetate:methanol (1:1:0.1). The appropriate fractions were collected and the solvent was removed to give 2.6 g (70%) of product, mp 168°–170°.

ANALYSIS:
Calculated for $C_{27}H_{44}N_2O_8$: 61.79%C, 8.47%H, 5.34%N,
Found: 61.94%C, 8.89%H, 5.54%N

EXAMPLE 60

8,13-Epoxy-7β-[N-(2-oxopropyl)aminocarbonyloxy-1α,6β,9α-trihydroxylabd-14-en-11-one-1,9-dimethylformamide acetal A solution of 0.6 ml oxalyl chloride in 15 ml of methylene chloride was stirred under nitrogen in a dry ice acetone bath. A mixture of 1.02 ml of dimethylsulfoxide and 3 ml of methylene chloride was added dropwise at a rate such the temperature did not exceed −50°. After stirring for 2 mins, 3 0 g of 8,13-epoxy-7β-[N-(2-hydroxypropyl)aminocarbonyloxy-1α,6β,9α-trihydroxylabd-14-en-11-one-1,9-dimethylformamide acetal in 6 ml of methylene chloride was added over a period of 5 mins. The mixture was stirred at −60° for 15 mins and 4.2 ml of triethylamine was added. The mixture was allowed to warm to room temperature, diluted with 50 ml of methylene chloride and washed with water, 0.01 N hydrochloric acid and saturated sodium bicarbonate solution. The organic layer was dried ever anhydrous sodium sulfate and the solvent was removed under reduced pressure. The residue was chromatographed on silica gel. The column was eluted with hexane:ethyl acetate:methanol (1:1:0.1). The appropriate fractions were collected and the solvent was removed to give 2.07 g (69.5%) of product, mp 173°–174°.

ANALYSIS:
Calculated for $C_{27}H_{42}N_2O_8$: 62.03%C, 8.12%H, 5.36%N,

Found: 61.98%C, 8.09%H, 5.16%N

EXAMPLE 61

7β-(Aminocarbonyloxy)-8,13-epoxy-1α,6β,9α-trihydroxylabd-14-en-11-one-1,9-carbonate To a stirred solution of 1.5 g of 7β-(aminocarbonyloxy)-8,13-epoxy-1α,6β,9α-trihydroxylabd-14-en-11-one in 50 ml of methylene chloride was added 708 mg of 1,1'-carbonyldimidazole followed by 441 mg of triethylamine. The mixture was stirred overnight at room temperature under a nitrogen atmosphere. After 16 hrs, the mixture was diluted with 50 ml of methylene chloride, washed with water and dried over anhydrous sodium sulfate, and filtered. The methylene chloride was evaporated under reduced pressure and the residue was chromatographed on silica gel. The column was eluted with hexane:ethyl acetate (1:1). The appropriate fractions were collected and the solvent was removed to give 0.9 g (57.2%) of product, mp 103°.
ANALYSIS:
Calculated for $C_{22}H_{31}NO_8$: 60.39%C 7.16%H 3.20%N,
Found: 60.17%C, 7.17%H, 3.20%H

EXAMPLE 62

8,13-7β-(N-propionylaminocarbonyloxy)-1α,6β,9α-trihydroxylabd-14-en-11-one-1,9-carbonate 7β-(Aminocarbonyloxy)-1α,6β,9α-trihydroxylabd-14-en-11-one-1,9-carbonate (2.2 g) was dissolved in 10 ml of propionic anhydride and a drop of concentrated sulfuric acid was added. The mixture was stirred at room temperature under an atmosphere of nitrogen. The mixture was diluted with saturated sodium bicarbonate solution and extracted with ether. The ether extracts were dried over anhydrous sodium sulfate, filtered, add the solvent was removed under vacuum. The residue was chromatographed on silica gel. The column was eluted with hexane:ethyl acetate (3:1) followed by hexane:ethyl acetate (1:1). The appropriate fractions were collected and the solvent was removed to give 2.0 g (81%) of product, mp 135°.
ANALYSIS:
Calculated for $C_{25}H_{35}NO_9$: 60.83%C, 7.16%H, 2.84%N
Found: 60.75%C, 7.23%H, 2.64%N

EXAMPLE 63

7β-(Aminocarbonyloxy)-1α-(N-t-butylaminoacetoxy)-6α,9β-dihydroxy-8,13-epoxylabd-14-en-11-one hydrochloride hydrate 7β-(Aminocarbonyloxy)-8,13-epoxy-1α,6β,9α-trihydroxylabd-14-en-11-one (250 mg) was dissolved in 3 ml of dichloromethane and 84.8 ul (81.1 mg) of dimethylaniline at 5°. A solution of 64.1 ul (148.4 mg) of bromoacetyl bromide in 2 ml of dichloromethane was added to the chilled solution over 15 mins and the solution was stirred for 1 hr at that temperature. The reaction mixture was warmed to room temperature and poured into a mixture of ice, water and ethyl acetate. The aqueous layer was extracted several times with ethyl acetate. The organic extracts were washed with saturated aqueous bicarbonate solution, dried over anhydrous sodium sulfate, filtered, and evaporated. The residue was dissolved in 2 ml ethyl acetate and the solution was stirred at ambient temperature under nitrogen. A solution of 129 ul of t-butylamine (178 mg) dissolved in 2 ml of ethyl acetate was added, after which the mixture was stirred overnight. The reaction mixture was poured into saturated aqueous sodium bicarbonate solution and extracted with ethyl acetate. The combined organic extracts were dried over anhydrous sodium sulfate, filtered and evaporated. The residue was flash chromatographed on silica gel in hexane:ethyl acetate:methanol (10:10:0.1). The appropriate fractions were combined and evaporated. The residue was dissolved in ether, from which the hydrochloride salt was precipitated by treatment with hydrogen chloride. Filtration afforded 153.4 mg (43.7%) of product, mp 166°–179° (dec).
ANALYSIS:
Calculated for $C_{27}H_{44}N_2O_8 \cdot HCl \cdot H_2O$: 55.99%C, 8.20%H, 4.83%N,
Found: 55.61%C, 7.95%H, 4.52%N

EXAMPLE 64

1α-(N-t-Butylaminoacetoxy)-6β,9α-dihydroxy-7β-[N-(2,2-dimethylpropionyloxy)aminocarbonyloxylabd-8,13-epoxy-14-en-11-one hydrochloride To a stirred solution of 2.05 g of 8,13-epoxy-7β-[N-(2,2-dimethylpropionyloxy)aminocarbonyloxy]-1α,6β,-9α-trihydroxylabd-14-en-11-one in 10 ml of methylene chloride was added 0.52 g of dimethylaniline. The mixture was cooled to 4° and a solution of 0.94 g of bromoacetyl bromide in 10 ml of methylene chloride was added dropwise over a period of 0.5 hr. The mixture was stirred a 5° under a nitrogen atmosphere for an additional hour. After equilibrating to room temperature, the mixture was poured into 50 ml of saturated sodium bicarbonate solution/ice, and the mixture was diluted with 50 ml of methylene chloride, washed with saturated sodium bicarbonate solution and dried over anhydrous sodium sulfate, and filtered. The solvent was removed and the residue was dissolved in 20 ml of methylene chloride. A solution of 1.4 g of t-butylamine in 20 ml ethyl acetate was added and the resulting mixture was stirred overnight under nitrogen. The reaction mixture was diluted with methylene chloride, washed with saturated sodium bicarbonate solution and water and dried over anhydrous sodium sulfate. The solvent was removed and the residue was chromatographed on silica gel. The appropriate fractions were collected and concentrated. The residue was dissolved in ether and anhydrous hydrogen chloride was passed through the solution to give 375 mg (15%) of product, mp 98°–103°.
ANALYSIS:
Calculated for $C_{32}H_{53}N_2O_{10}Cl$: 58.12%C, 8.08%H, 4.20%N,
Found: 57.77%C, 8.34%H, 4.59%N

EXAMPLE 65

1α-(N-t-Butylaminoacetoxy)-6β,9α-dihydroxy-8,13-epoxy-7β-(N-methylaminocarbonyloxy)labd-14-en-11-one hydrochloride hydrate 8,13-Epoxy-7β-(N-methylaminocarbonyloxy)-8,13-epoxy-1α,6β,9α-trihydroxylabd-14-en-11-one (280 mg) was dissolved in 6 ml of dry dichloromethane and 95 ul (81.8 mg) of N,N-dimethylaniline. The mixture was stirred chilled to 5° under nitrogen. A solution of 69 ul (159.5 mg) of bromoacetyl bromide in 2 ml of dry dichloromethane was added over 15 min, after which the mixture was stirred for 1 hr. The reaction mixture was poured into chilled dilute sodium bicarbonate solution. The product was extracted into ethyl acetate, and the solution was dried over anhydrous sodium sulfate, filtered and evaporated. The residue was dissolved in 4 ml of ethyl acetate and 140 ul (192.4 mg) of t-butylamine.

The mixture was stirred at ambient temperature under nitrogen overnight, after which it was diluted with dichloromethane and washed with saturated aqueous sodium bicarbonate solution and saturated brine. After drying the mixture over sodium sulfate and filtration, the solvent was removed by evaporation. The residue was flash chromatographed on silica gel in hexane:ethyl acetate:methanol (10:10:0). The appropriate fractions were combined and evaporated. The residue was dissolved in ether from which the hydrochloride was precipitated by treatment with hydrogen chloride. Filtration afforded 192 mg (54.2%) of product, mp 163°–187° (dec).
ANALYSIS:
Calculated for $C_{28}H_{49}ClNO_9$: 56.69%C, 8.34%H, 4.72%N,
Found: 56.68%C, 8.10%H, 4.68%N

EXAMPLE 66

7β-[N-(N-Acetylglycyloxy)aminocarbonyloxy]-8,13-epoxy-1α,6β,9α-trihydroxylabd-14-en-11-one To a stirred solution of 246 mg of N-acetylglycine in 25 ml of dimethylformamide was added 340 mg of 1,1′-carbonyldiimidazole. The mixture was stirred for 45 mins at room temperature under a nitrogen atmosphere. 8,13-Epoxy-7β-(hydroxyaminocarbonyloxy)-1α,6β,9α-trihydroxylabd-14-en-11-one (750 mg) dissolved in 25 ml of dimethylformamide was added and the reaction mixture was stirred overnight. The mixture was diluted with water and extracted with methylene chloride. The methylene chloride extracts were washed repeatedly with water, dried over anhydrous sodium sulfate and filtered. The solvent was removed and the residue was crystallized from cyclohexane to give 510 mg (55%) of product, mp 55°.
ANALYSIS:
Calculated for $C_{24}H_{38}N_2O_{10}$: 57.01%C, 7.29%H, 5.32%N,
Found: 57.35%C, 7.57%H, 5.37%M

EXAMPLE 67

7β-[N-(4-Dimethylaminobutyryloxy)aminocarbonyloxy]-8,13-epoxy-1α,6β,9α-trihydroxylabd-14-en-11-one hydrochloride hydrate To a stirred suspension of 469 mg of 4-dimethylaminobutyric acid hydrochloride in 25 ml of methylene chloride was added 282 g of triethylamine, and the mixture was stirred for 0.5 hr at room temperature under a nitrogen atmosphere. 1,1′-Carbonyldiimidazole (455 mg) was added and the mixture stirred for 45 mins before the addition of a solution of 1.0 g of 8,13-epoxy-7β-(hydroxyaminocarbonyloxy)-1α,6β,9α-trihydroxylabd-14-en-11-one in 5 ml of tetrahydrofuran and 25 ml of methylene chloride. After stirring 16 hrs, the mixture was washed with water, 0.01 N hydrochloric acid and saturated sodium bicarbonate solution, dried over anhydrous sodium sulfate, filtered and concentrated under reduced pressure. The residue was dissolved in anhydrous ether and ethereal hydrogen chloride was added until the pH was neutral. The precipitate was filtered and dried to give 710 mg (51.8%) of product, mp 125°–130°.
ANALYSIS:
Calculated for $C_{27}H_{44}N_2O_9$: 54.47%C, 7.97%H, 4.71%N,
Found: 54.60%C, 7.96%H, 4.50%N

EXAMPLE 68

8,13-Epoxy-7β-[N-(2-piperidinoethyl)aminocarbonyloxy-1α,6β,9α-trihydroxylabd-14-en-11-one hydrochloride hydrate A solution of 1.23 g of 8,13-epoxy-7β-[N-(2-piperidinoethyl)aminocarbonyloxy)-1α,6β,9α-trihydroxylabd-14-en-11-one 1,9-dimethylformamide acetal in 50 ml of 3/1 methanol/water was stirred at 60°–70° under nitrogen for 40 hr. The solution was allowed to cool to room temperature and concentrated. The residue was dissolved in a minimum volume of 10% tetrahydrofuran/dichloromethane and flash chromatographed on silica gel (eluent: 10% tetrahydrofuran/dichloromethane, 15% tetrahydrofuran/dichloromethane, 20% tetrahydrofuran/dichloromethane and 25% tetrahydrofuran/dichloromethane). The appropriate fractions were combined and concentrated. The residue was dissolved in anhydrous ether, dried over anhydrous sodium sulfate, filtered. The hydrochloride salt was precipitated by addition of ethereal hydrogen chloride. The salt was collected and dried at 80° (2 mm) for 2 hr to give 0.62 g (50.2%) of product, mp 156°–191°.
ANALYSIS:
Calculated for $C_{28}H_{46}N_2O_7 \cdot HCl \cdot H_2O$: 58.27%C, 8.56%H, 4.85%N,
Found: 58.07%C, 8.63%H, 4.88%N

EXAMPLE 69

7β-[N-(2-Dimethylaminoethyl)aminocarbonyloxy]-8,13-epoxy-1α,6β,9α-trihydroxylabd-14-en-11-one-1,9-dimethylformamide acetal To a stirred solution of 3.0 g of 8,13-epoxy-1α,6β,9α-trihydroxylabd-14-en-11-one-1,9-dimethylformamide acetal in 60 ml of methylene chloride was added 1.38 g of 1,1′-carbonyldiimidazole. The mixture was stirred overnight under a nitrogen atmosphere at room temperature. N,N-Dimethylethylenediamine (4.7 ml) was added and the reaction mixture was washed with 0.01 N hydrochloric acid until the washings remain neutral. The organic portion was dried over anhydrous sodium sulfate, filtered, the solvent removed, and the residue chromatographed on silica gel. The column was eluted with 10% methanol/methylene chloride. The appropriate fractions were combined and the solvent removed under reduced pressure. The residue was crystallized from cyclohexane to give 2.3 g (60%) of product, mp 162°–163°.
ANALYSIS:
Calculated for $C_{28}H_{47}N_3O_7$: 62.53%C, 8.83%H, 7.81%N,
Found: 62.77%C, 8.87%H, 7.63%N

EXAMPLE 70

8,13-Epoxy-7β-[N-(2-piperidinoethyl)aminocarbonyloxy)-1α,6β,9α-trihydroxylabd-14-en-11-one-1,9-dimethylformamide acetal To a stirred solution of 3.0 g of 8,13-epoxy-1α,6β,7β,9α-trihydroxylabd-14-en-11-one-1,9-dimethylformamide acetal in 60 ml of ethyl acetate was added 1.38 g of 1,1′-carbonyldiimidazole. The solution was stirred overnight at room temperature. To the solution was added 1.01 ml (0.909 g) of 2-aminoethylpiperidine. The solution was poured into ice/ethyl acetate/water, extracted twice with ethyl acetate, twice with water, once with saturated sodium chloride solution, dried over anhydrous sodium sulfate, and filtered. The filtrate was evaporated. The residue was dissolved in 5% methanol/dichloromethane and flash chromatographed on silica gel, eluting with 5% methanol/dichloromethane. The appropriate fractions were combined, concentrated and dried at 110° (2 mm) to provide 2.48 g (36.1%) of product, as a glass.
ANALYSIS:
Calculated for $C_{31}H_{51}N_3O_7$: 64.44%C, 8.90%H, 7.27%N,
Found: 64.14%C, 9.04%H, 7.17%N

EXAMPLE 71 b 8,13-Epoxy-6β-(hydroxylaminocarbonyloxy)-1α,7β,-9α-trihydroxylabd-14-en-11-one To a stirred solution of 2.0 g of 8,13-epoxy-7β-(hydroxyaminocarbonyloxy)-1α,7β,9α-trihydroxylabd-14-en-11-one in 75 ml of tertiary-butyl alcohol and 5 ml of tetrahydrofuran at 0° was added 7.0 g of potassium tertiary-butoxide. The mixture was stirred at 0° for 1 hr and slowly warmed to room temperature. After stirring at room temperature for 1 hr the reaction mixture was poured into ice/water and extracted with ethyl acetate. The extracts were combined and dried over anhydrous sodium sulfate, the solvent removed and the residue chromatographed on silica gel. The column was eluted with hexane/ethyl acetate (1:1) followed by ethyl acetate. The appropriate fractions were collected and the solvent removed to give 300 mg of product, mp 155°–160°.
ANALYSIS:
Calculated for $C_{21}H_{33}NO_8$: 58.99%C, 7.80%H, 3.27%N,
Found: 58.52%C, 8.05%H, 3.12%N

EXAMPLE 72

8,13-Epoxy-7β-[1-(methylpiperazin-4-yl)carbonyloxy]-1α,6β,9α-trihydroxylabd-14-en-11-one To a stirred solution of 5.0 g of 8,13-epoxy-1α,6β7β,-9α-trihydroxylabd-14-en-11-one-1,9-dimethylformamide acetal in 100 ml of dichloromethane was added 2.15 g of 1,1′-carbonyldiimidazole. The solution was stirred under nitrogen for 20 hr. To the solution was added 1.3 g of 1-methylpiperazine. The solution was stirred under nitrogen for 72 hr. The solution was poured into water/ice/ethyl acetate, extracted twice with ethyl acetate, washed with water and saturated sodium chloride solution. The ethereal solution was dried over anhydrous sodium sulfate, filtered and concentrated. The residue was dissolved in ethyl acetate and flash chromatographed on silica gel, eluting with ethyl acetate followed by 30% tetrahydrofuran/ethyl acetate. The appropriate fractions were combined and concentrated. Recrystallization from hexanes provided 1.81 g of product, mp 209°–215°.
ANALYSIS:
Calculated for $C_{29}H_{47}N_3O_7$: 63.36%C, 8.62%H, 7.65%N,
Found: 63.52%C, 8.64%H, 7.56%N

EXAMPLE 73

8,13-Epoxy-7β-[N-2-(pyridin-2-ylethyl)aminocarbonyloxy]-1α,6β,9α-trihydroxylabd-14-en-11-one-1,9-dimethylformamide acetal To 5.05 g of 8,13-epoxy-1α,6β,7β,9α-tetrahydroxylabd-14-en-11-one-1,9-dimethylformamide acetal was added 100 ml of dry dichloromethane under nitrogen. To the solution was added 2.17 g of 1,1′-carbonyldiimidazole and the solution was stirred for 18 hrs, after which 1.6 ml of 2(2-aminoethyl)pyridine was added, and the reaction mixture was stirred for 18 hrs. The reaction mixture was poured into ice/water/ether, extracted with ether, washed with water and saturated sodium chloride solution, dried over anhydrous sodium sulfate, filtered and concentrated. The residue was flash chromatographed, employing 50% ethyl acetate/hexane. The appropriate fractions were combined and again flash chromatographed using 25% acetone/hexane to provide 2.80 g (42%) of product, mp 159°.
ANALYSIS:
Calculated for $C_{31}H_{44}N_3O_7$: 65.12%C, 7.93%H, 7.35%N,
Found: 65.22%C, 7.90%H, 7.30%N

EXAMPLE 74

7β-[N-3-(Dimethylaminopropyl)aminocarbonyloxy]-1α,6β,9α-trihydroxylabd-14-en-11-one-1,9-dimethylformamide acetal To a stirred solution of 3.0 g of 1α,6β,7β,9α-tetrahydroxylabd-14-en-11-one-1,9-dimethylformamide acetal in 60 ml of methylene chloride was added 1.38 g of 1,1′-carbonyldiimidazole and the mixture was stirred overnight under a nitrogen atmosphere at room temperature. 3-Dimethylaminopropylamine (3.6 g) was added and the mixture was stirred an additional 24 hrs. The reaction mixture was washed with 0.01 N hydrochloric acid until the washings remained acidic. The organic layer was dried over anhydrous sodium sulfate, filtered and the solvent was evaporated. The residue was purified by flash chromatography. The column was eluted with 10% methanol/methylene chloride. The appropriate fractions were collected, the solvent was evaporated and the residue was crystallized from cyclohexane to give 2.75 g (70%) of product, mp 160°.
ANALYSIS:
Calculated for $C_{29}H_{49}N_3O_7$: 63.12%C, 8.97%H, 7.62%N,
Found: 62.47%C, 8.93%H, 7.45%N

EXAMPLE 75

8,13-Epoxy-7β-[N-2-(pyridylmethyl)aminocarbonyloxy]-1α,7β,9α-trihydroxylabd-14-en-11-one-1,9-dimethylformamide acetal To 5.00 g of 8,13-epoxy-1α,6β,7β,9α-tetrahydroxylabd-14-en-11-one-1,9-dimethylformamide acetal was added 100 ml of dry dichloromethane under nitrogen. To the solution was added 2.15 g of 1,1-′carbonyldiimidazole and the solution was stirred for 18 hrs. To the solution was added 1.37 ml of 2-(aminomethyl)pyridine and the solution was stirred for an additional 48 hrs. The solution was then poured ice/water/ethyl acetate, extracted with ether, washed with water and saturated sodium chloride, dried with anhydrous sodium sulfate, filtered and concentrated. The residue was flash chromatographed employing 50% ethyl acetate/hexane. The appropriate fractions were combined and again flash chromatographed, employing 25% acetone/hexane to provide 5.46 g (83%) of product. Recrystallization from ether/hexane provided the analytical product, mp 113°–114°.
ANALYSIS:
Calculated for $C_{30}H_{43}N_3O_7$: 64.61%C, 7.77%H, 7.53%N, Found: 64.495C, 7.825H, 7.30%N

EXAMPLE 76

6β-[N-(3-Dimethylaminopropyl)aminocarbonyloxy]-1α,7β,9α-trihydroxylabd-14-en-11-one-1,9-dimethylformamide To a stirred solution of 2.5 g of 8,13-epoxy-1α,6β,7β,-9α-trihydroxylabd-14-en-11-one-6,7-carbonate-1,9-dimethylformamide acetal in 10 ml of methylene chloride was added 8.2 g of 3-dimethylaminopropylamine. The mixture was stirred at room temperature for 48 hrs. The mixture was diluted with methylene chloride and extracted with 0.01 N hydrochloric acid until the extracts were neutral. The methylene chloride layer was dried over anhydrous sodium sulfate, filtered add the solvent was evaporated under reduced pressure. The residue was purified by flash chromatography. The column was eluted 10% methanol/methylene chloride. The appropriate fractions were isolated and the solvent evaporated to give 1.7 g (55.4%) of product, mp 130°–132°.
ANALYSIS:
Calculated for $C_{29}H_{49}N_3O_7$: 63.12%C, 8.97%H, 7.62%N,
Found: 63.21%C, 9.04%H, 7.54%N

EXAMPLE 77

8,13-Epoxy-6β-(4-methylpiperazinyl)carbonoxy-1α,7β,9α-trihydroxylabd-14-en-11-one-1,9-dimethylformamide acetal To a stirred solution of 3.0 g of 8,13-epoxy-1α,6β,7β,-9α-tetrahydroxylabd-14-en-11-one-6,7-carbonate-1,9-dimethylformamide acetal in 5 ml of methylene chloride was added 15 ml of 1-methylpiperazine. The mixture was stirred 16 hrs under a nitrogen atmosphere. The mixture was diluted with methylene chloride and extracted with 0.01N hydrochloride acid until the washings were neutral. The organic layer was dried over anhydrous sodium sulfate, filtered and the solvent was evaporated. The residue was chromatographed on silica gel, eluting with 10% methanol/dichloromethane. The appropriate fractions were collected and the solvent was evaporated to give 2.56 g (70.5%) of product.
ANALYSIS:
Calculated for $C_{29}H_{47}N_3O_7$: 63.35%C, 8.63%H, 7.64%N,
Found: 63.46%C, 8.66%H, 7.70%N

EXAMPLE 78

8,13-Epoxy-6β-(4-pyridylmethyl)aminocarbonyloxy-1α,7β,9α-trihydroxylabd-14-en-11-one-1,9-dimethylformamide acetal To a stirred solution of 2.5 g of 8,13-epoxy-1α,6β,7β,-9α-tetrahydroxylabd-14-en-11-one-6,7-carbonate-1,9-dimethylformamide acetal in 10 ml of methylene chloride was added 5 ml of 4-(aminomethyl)pyridine. The mixture was diluted with methylene chloride and extracted with 0.01 N hydrochloric acid until the washings were acidic. The organic layer was dried over anhydrous sodium sulfate, filtered and the solvent was evaporated. The residue was flash chromatographed on silica gel, eluting with 10% methanol/dichloromethane, The appropriate fractions were collected and the solvent was evaporated to give 1.7 g (55%) of product, mp 145°–147°.
ANALYSIS:
Calculated for $C_{30}H_{43}N_3O_7$: 64.60%C, 7.78%H, 7.53%N,
Found: 64.51%C, 7.81%H, 7.43%N

EXAMPLE 79

8,13-Epoxy-6β-[N-2-(pyridylmethyl)aminocarbonyloxy]-1α,7β,9α-trihydroxylabd-14-en-11-one-1,9-dimethylformamide acetal To a stirred solution of 2.5 g of 8,13-epoxy-1α,6β,7β,-9α-trihydroxylabd-14-en-11-one-6,7-carbonate-1,9-dimethylformamide acetal in 10 ml of methylene chloride was added 5 ml of 2-(aminomethyl)pyridine. The mixture was stirred for 73 hrs at room temperature. The reaction mixture was repeatedly extracted with 0.01 N hydrochloric acid until the washings became acidic. The organic phase was dried over anhydrous sodium sulfate, filtered and the solvent was evaporated. The residue was chromatographed on silica gel. The column was eluted with 10% methanol/dichloromethane. The appropriate fractions were collected and the solvent was evaporated to give 1.9 g (60.9%) of product, mp 90°–93°.
ANALYSIS:
Calculated for $C_{30}H_{43}N_3O_7$: 64.60%C, 7.78%H, 7.53%N,
Found: 64.61%C, 7.77%N, 7.55%N

EXAMPLE 80

8,13-Epoxy-7β-[N-2-(pyridylmethyl)aminocarbonyloxy]-1α,6β,9α-trihydroxylabd-14-en-11-one hydrochloride hydrate To 4.89 g of 8,13-epoxy-7β-[N-2-(pyridinylmethyl)aminocarbonyloxy]-1α,6β,9α-trihydroxylabd-14-en-11-one-1,9dimethylformamide acetal was added 196 ml of a 3/1 mixture of methanol/water. The solution was stirred at 60°–70° for 48 hrs. The solution was then concentrated. The residue was flash chromatographed, employing 35% acetone/hexane, and the appropriate fractions were combined and concentrated. The residue was dissolved in ether and etheral hydrochloride was added. The precipitate was filtered and dried at 110° for 2 hrs to provide 2.27 g (48%) of product, mp 178°–180°.
ANALYSIS:
Calculated for $C_{27}H_{41}ClN_2O_8$: 58.21%C, 7.42%H, 5.03%N,
Found: 57.96%C, 7.12%H, 4.98%N

EXAMPLE 81

8,13-Epoxy-7β-methylpiperazino)carbonyloxy-1α,6β,-9α-trihydroxylabd-14-en-11-one A solution of 1.84 g of 8,13-epoxy-7β-(4-methylpiperazino)carbonyloxy-1α,6β,9α-trihydroxylabd-14-en-11-one-1,9-dimethylformamide acetal in 80 ml of methanol/water (3/1) was stirred at 60°–70° for 48 hr under nitrogen. The suspension was allowed to cool to room temperature. The precipitate was collected by filtration and dried at 40° (2 mm) for 3 hr to provide 0.94 g (56.9%) of product, mp 254°–259°.
ANALYSIS:
Calculated for $C_{26}H_{42}N_2O_7$: 63.13%C, 8.56%H, 5.67%N,
Found: 63.26%C, 8.55%H, 5.68%N

EXAMPLE 82

8,13-Epoxy-7β-[N-(3-dimethylaminopropyl)-aminocarbonyloxy]-1α,6β,9α-trihydroxylabd-14-en-11-one hydrochloride hydrate 8,13-Epoxy-7β-[N-(3-dimethylaminopropyl)aminocarbonyloxy]-1α,6β,9α-trihydroxylabd-14-en-11-one-1,9-dimethylformamide acetal (1.5 g) was dissolved in 50 ml of methanol and 16 ml of water. The mixture was heated at 60° for 72 hrs and allowed to cool. The reaction mixture was extracted with ethyl acetate and ethyl acetate extracts were washed with saturated sodium chloride solution, dried over anhydrous sodium sulfate, and filtered. The solvent was removed under reduced pressure and the residue was chromatographed on silica gel, The column was eluted with 10% methanol/dichloromethane. The appropriate fractions were isolated and the solvent was evaporated. The residue was dissolved in ether and ethereal hydrogen chloride was added. The hydrochloride salt was dried under vacuum to give 575 mg (40%) of product, mp 147°-150°.
ANALYSIS:
Calculated for $C_{26}H_{47}ClN_2O_8$: 56.55%C, 8.61%H, 5.08%N,
Found: 56.46%C, 8.43%H, 5.08%N

EXAMPLE 83

8,13-Epoxy-7β-[N-(2-dimethylaminoethyl)aminocarbonyloxy]-1α,6β,9α-trihydroxylabd-14-en-11-one hydrochloride 8,13-Epoxy-7β-[N-(2-dimethylaminoethyl)aminocarbonyloxy]-1α,6β,9α-trihydroxylabd-14-en-11-one-1,9-dimethylformamide acetal (1.5 g) was dissolved in 50 ml of methanol and 16 ml of water. The resulting mixture was heated at 55°-60° for 96 hrs. The reaction mixture was allowed to cool to room temperature, extracted with ethyl acetate and the ethyl acetate extracts were washed with saturated sodium chloride. The organic layer was dried over anhydrous sodium sulfate, filtered and the solvent was evaporated. The residue was chromatographed on silica gel. The column was eluted with 40% methanol/methylene chloride. The appropriate fractions were collected and the solvent was evaporated. The residue was dissolved in a minimum amount of tetrahydrofuran, diluted with ether and ethereal hydrogen chloride was added to give, 660 mg (45%) of product, mp 240°.
ANALYSIS:
Calculated for $C_{25}H_{43}ClN_2O_7$: 57.83%C, 8.36%H, 5.39%N,
Found: 57.74%C, 8.53%H, 5.46%N

EXAMPLE 84

8,13-Epoxy-7β-[N-2-(2-pyridinylethyl)aminocarbonyloxy]-1α,6β,9α-trihydroxylabd-14-en-11-one hydrochloride To 1.94 g of 7β-[N-2-(2-pyridinylethyl)aminocarbonyloxy]1α,6β,9α-trihydroxylabd-14-en-11-one-1,9-dimethylformamide acetal was added 78 ml of a 3/1 mixture of methanol/water. The solution was stirred at 60°-70° under nitrogen for 65 hrs. The solution was concentrated. The residue was flash chromatographed, employing 30% acetone/hexane. To 0.78 g of the residue (1.20 g) dissolved in ether was added ethereal hydrogen chloride. The precipitate was collected and dried at 110° for 2 hrs to provide 0.64 g (52%) of product, mp 172°.
ANALYSIS:
Calculated for $C_{28}H_{41}ClN_2O_7$: 60.80%C, 7.47%N, 5.07%N,
Found: 60.62%C, 7.59%H, 5.04%N,

EXAMPLE 85

8,13-Epoxy-6β-[4-(pyridinylmethyl)aminocarbonyloxy]-1α,7β,9α-trihydroxylabd-14-en-11-one 6β-[4-Pyridylmethyl)aminocarbonyloxy-1α,7β,9α-trihydroxylabd-14-en-11-one-1,9-dimethylformamide acetal (1.2 g) was dissolved in 50 ml of methanol and 16 ml of water. The mixture was heated at 60° for 96 hrs and allowed to cool to room temperature. The mixture was extracted with methylene chloride. The extracts were dried over anhydrous sodium sulfate, filtered, and the solvent was evaporated. The residue was crystalized from hexane/ethyl acetate to give 1.04 g (95%) of product, mp 240°.
ANALYSIS:
Calculated for $C_{27}H_{38}N_2O_7$: 64.51%C, 7.63%H, 5.57%N,
Found: 64.385C, 7.67%H, 5.62%N

EXAMPLE 86

8,13-Epoxy-6β-(4-methylpiperazinylcarbonyloxy)-1α,7β,9α-trihydroxylabd-14-en-11-one hydrochloride 8,13-Epoxy-6β-(4-methylpiperazinylcarbonyloxy)-1α,7β,9α-trihydroxylabd-14-en-11-one-1,9-dimethylformamide acetal (2.3 g) was dissolved in 50 ml of methanol and 15 ml of water. The mixture was heated at 60° for 72 hrs. The mixture was cooled to room temperature and stirred overnight. The precipitate was collected and dried to give 1.65 g (79%)of product. A portion of the precipitate (350 mg) was dissolved in ether and etheral hydrogen chloride was added until solution became acidic. The hydrochloride had mp>260°.
ANALYSIS:
Calculated for $C_{26}H_{43}ClN_2O_7$: 58.78%C, 8.18%H, 5.27%N,
Found: 58.79%C, 8.22%H, 5.13%N

EXAMPLE 87

8,13-Epoxy-7β-[N-(2-methylacryloyoxy)aminocarbonyoxy]-1α,6β,9α-trihydroxylabd-14-en-11-one To a stirred solution of 240 mg of methylacrylic acid in 50 ml of methylene chloride was added 283 mg of triethylamine. The mixture was cooled to 0° in an ice-/water bath and stirred for 0.5 hr after 332 mg of trimethylacetyl chloride was added. 8,13-Epoxy-7β-(hydroxyaminocarbonyloxy)-1α,6β,9α-trihydroxylabd-14-en-11-one (1.10 g) and 34 mg of 4-dimethylaminopyridine dissolved in 10 ml of tetrahydrofuran and 50 ml of methylene chloride was added to the reaction mixture. The mixture was stirred for 1 hr at 0°, washed with water, 0.01 N hydrochloric acid and saturated sodium bicarbonate solution. The organic layer was dried over anhydrous sodium sulfate, filtered and the solvent was evaporated. The residue was chromatographed on silica gel. The column was eluted with hexane ethyl acetate (2/1). The appropriate fractions were collected and the solvent was evaporated to give 550 mg (48%) of product, mp 103°-106°.
ANALYSIS:

Calculated for $C_{25}H_{37}NO_9$: 60.57%C, 7.54%H, 2.83%N,
Found: 60.70%C, 7.62%H, 2.66%N

EXAMPLE 88

8,13-Epoxy-7β-[N-methyl-N-(4-methylpiperidinyl)carbonyloxyaminocarbonyloxy]-1α,6β,9α-trihydroxylabd-14-en-11-one hydrochloride hydrate To a stirred suspension of 242 mg of 4-methylpiperidin-4-ylcarboxylic acid in 25 ml of methylene chloride was added 0.2 ml of triethyl amine. The mixture was stirred for 0.5 hr before 220 mg of 1,1'-carbonyldiimidazole was added. After stirring under nitrogen for an additional 45 mins, 8,13-epoxy-7β-(hydroxyaminocarbonyloxy)-1α,6β,9α-trihydroxylabd-14-en-11-one (500 mg) in 25 ml of methylene chloride was added dropwise. The mixture was stirred for 16 hrs. The reaction mixture was washed with 0.01 N hydrochloric acid, saturated sodium bicarbonate solution and water. The organic layer was dried over anhydrous sodium sulfate, filtered and the solvent was evaporated. The residue dissolved in ether, and ethereal hydrogen chloride was added to the solution. The precipitate was collected and dried at 60° under vacuum to give 265 mg (377%) of product, mp 174°.

ANALYSIS:
Calculated for $C_{29}H_{49}ClN_2O_{10}$: 56.05%C, 7.96%H, 4.51%N,
Found: 55.97%C, 7.92%H, 4.57%N

EXAMPLE 89

7β-[N-(3-Dimethylaminopropionyloxy)aminocarbonyloxy]-1α,6β,9α-trihydroxylabd-14-en-11-one hydrochloride hydrate To a stirred solution of 2.0 g of 8,13-epoxy-7β-(hydroxyaminocarbonyloxy)-1α,6β,9α-trihydroxylabd-14-en-11-one, 0.57 g of triethylamine in 50 ml of dichloromethane and 10 ml of tetrahydrofuran at 0° was added 57 mg of 4-dimethylaminopyridine, followed by 711 mg of 3-chloropropionyl chloride in 50 ml of dichloromethane. The reaction mixture was stirred at 0° for 3.0 hrs and a room temperature for 15 hrs. The reaction mixture was washed with 0.01 N hydrochloric acid (2×20 ml), saturated sodium bicarbonate solution, and water. The organic layer was dried over anhydrous sodium sulfate, filtered, and the solvent was evaporated under reduced pressure to provide 7β-[N-(3-chloropropionyloxy)aminocarbonyloxy]-1α,6β,9α-trihydroxylabd-14-en-11-one, after flash chromatography on silica gel, eluting the column with hexane/ethyl acetate (2:1).

To a stirred suspension of 75.6 mg of dimethylamine hydrochloride in 5 ml of dichloromethane was added 187 mg of triethylamine. The solution was added to a stirred mixture of 400 mg of 7β-[N-(3-chloropropionyloxy)aminocarbonyloxy]-1α,6β,9α-trihydroxylabd-14-en-11-one in 10 ml of methylene chloride and 0°. The mixture was stirred for 0.5 hr under a nitrogen atmosphere. The mixture was then diluted with dichloromethane, and the solution was washed with water, 0.01 N hydrochloric acid and saturated sodium bicarbonate solution. The organic phase was dried over anhydrous sodium sulfate, filtered and the filtrate was evaporated. The residue was dissolved in ether and ethereal hydrogen chloride was added to provide 230 mg (53%) of product, mp 144°-146°.

ANALYSIS:
Calculated for $C_{26}H_{45}ClN_2O_{10}$: 53.72%C, 7.64%H, 4.82%N,
Found: 53.71%C, 7.78%H, 4.79%N

EXAMPLE 90

7β-[N-(trans-3-Chloroacryloyloxy)aminocarbonyloxy]-8,13-epoxy-1α,6β,9α-trihydroxylabd-14-en-11-one hydrochloride To a stirred solution of 298 mg of trans-3-chloroacrylic acid in 50 ml of methylene chloride at 0° was added 282 mg of triethylamine followed by 332 mg of trimethylacetyl chloride. The reaction mixture was stirred at 0° under a nitrogen atmosphere for 0.5 hr and then 1.0 g of 8,13-epoxy-7β-(hydroxyaminocarbonyloxy)-1α,6β,9α-trihydroxylabd-14-en-11-one dissolved in 10 ml of tetrahydrofuran and 50 ml of methylene chloride was added. The mixture was stirred overnight at room temperature. 4-Dimethylaminopyridine (34 mg) was added and the mixture was stirred an additional 2.5 hrs. The mixture was washed with water, 0.01 N hydrochloric acid and saturated sodium bicarbonate solution. The organic layer was dried over anhydrous sodium sulfate, filtered and the solvent evaporated under reduced pressure. The residue was chromatographed on silica gel. The column was eluted with hexane/ethyl acetate (2:1). The appropriate fractions were isolated and the solvent evaporated to give 300 mg (17.3%) of product, mp 105°-110°.

ANALYSIS:
Calculated for $C_{24}H_{34}ClNO_9$: 55.84%C, 6.65%H, 2.71%N,
Found: 55.57%C, 6.77%H, 2.54%N

EXAMPLE 91

8,13-Epoxy-7β-(N-methylaminocarbonyloxy)-1α,6β,9α-trihydroxylabd-14-en-11-one-1,9-carbonate To a stirred solution of 5.0 g of 8,13-epoxy-7β-(N-methylaminocarbonyloxy)-1α,6β,9α-trihydroxylabd-14-en-11-one in 200 ml of pyridine at 0° was added dropwise a solution of 50 ml of 20% phosgene in toluene. The reaction mixture was stirred for 1 hr at 0° and allowed to warm to room temperature over 1 hr. The reaction mixture was poured into ice/ethyl acetate/water, extracted twice with ethyl acetate, washed with cold 5% hydrochloric acid until the washings were acidic, washed with saturated sodium chloride solution, dried over anhydrous sodium sulfate, filtered, and evaporated. To a stirred solution of the residue in 50 ml of dry pyridine at 0° was added dropwise a solution of 12.5 ml of 20% phosgene in toluene. The mixture was stirred at ice bath temperature for 0.5 hr and at room temperature for 0.5 hr. The reaction mixture was then poured into ice/water/ethyl acetate, extracted twice with ethyl acetate, washed with cold 5% hydrochloric acid until acidic, washed with saturated sodium chloride solution, dried over anhydrous sodium sulfate, filtered and concentrated. The residue was dissolved in a minimum volume of ethyl acetate and flash chromatographed on silica gel, eluting with 30% ethyl acetate/hexane followed by 40% ethyl acetate/hexanes. Concentration of the appropriate fractions provided 4.19 g (79.2%) of product. Several milligrams of the material was recrystallized from ethyl acetate/cyclohexane to provide the analytical product having mp 137°-141°.

EXAMPLE 92

8,13-Epoxy-6β,7β-bis(1-imidazoloylcarbonyloxy)-1α,9α-dihydroxylabd-14-en-11-one-1,9-dimethylformamide acetal To a stirred solution of 3.0 of 8,13-epoxy-1α,6β,7β,-9α-tetrahydroxylabd-14-en-11-one-1,9-dimethylformamide acetal in 60 ml of ethyl acetate was added 2.76 g of 1,1'-carbonyldiimidazole. The solution was stirred at room temperature overnight. The solution was concentrated. The residue was dissolved in ethyl acetate and flash chromatographed on silica gel, eluting with 60% ethyl acetate/hexane, followed by 80% ethyl acetate/hexane. The appropriate fractions were combined and concentrated to provide 2.26 g (52%) of product, mp 110°.

ANALYSIS:
Calculated for $C_{31}H_{41}N_5O_8$: 60.87%C, 6.76%H, 11.45%N,
Found: 60.42%C, 6.88%H, 11.32%N

EXAMPLE 93

8,13-Epoxy-7β-[N,N-bis(2-hydroxyethylamino)carbonyloxy-1α,6β,9α-trihydroxylabd-14-en-11-one A solution of 0.2 g of 8,13-epoxy-7β-[N,N-bis(2-hydroxyethylamino)carbonyloxy-1α,6β,9α-trihydroxylabd-14-en-11-one1,9-dimethylformamide acetal, 5 ml of methanol and 5 ml of 80% acetic acid was stirred at room temperature under nitrogen for 48 hr. The solution was diluted with ethyl acetate, washed twice with water and once with saturated sodium chloride solution. The solution was dried over anhydrous sodium sulfate, filtered and concentrated. The residue was dissolved in a minimum volume of 80% ethyl acetate/hexanes and flash chromatographed on silica gel. Concentration of the appropriate fractions provided 106 mg (59%) of product, mp 90°–113°.

ANALYSIS:
Calculated for $C_{25}H_{41}NO_9$: 60.10%C, 8.27%H, 2.80%N,
Found: 60.12%C, 8.29%H, 2.59%N

EXAMPLE 94

8,13-Epoxy-1α,6β,7β,9α-tetrahydroxylabd-14-en-11-one-6,7-carbonate 1,9-dimethylformamide acetal 8,13-Epoxy-1α,6β,7β,9α-tetrahydroxylabd-14-en-11-one-1,9-dimethylformamide acetal-1,9-dimethylformamide acetal (1.059 g) in 25 ml of toluene containing 0.50 g of 1,1'-carbonyldiimidazole and 0.55 ml of triethylamine was heated under reflux for 3 hr. The reaction mixture was evaporated and applied to a flash chromatography column. Elution with 50% ethyl acetate/hexane gave 0.976 g (87%) of product. An analytical sample obtained by recrystallization from hexane had mp 138°–140°.

ANALYSIS:
Calculated for $C_{24}H_{35}NO_7$: 64.12%C, 7.85%H, 3.12%N,
Found: 63.91%C, 7.98%H, 3.08%N

EXAMPLE 95

7β-Acetoxy-1α,9β-dihydroxy-6β-[N-(2-dimethylaminoethyl)aminocarbonyloxy]-8,13-epoxylabd-14-en-11-one-1,9-dimethylformamide acetal 5.07 of 8,13-epoxy-1α,6β,7β,9α-tetrahydroxylabd-14-en-11-one-1,9-dimethylformamide acetal in 100 ml of dichloromethane was added 2.33 g of 1,1'-carbonyldiimidazole and 3.4 ml of triethylamine. The solution was stirred for 24 hrs under nitrogen. After addition of 6.62 ml of N,N-dimethylethylenediamine, the solution was stirred for an additional 72 hrs under nitrogen. The solution was poured into a mixture of ice/water/ethyl acetate and extracted with ethyl acetate. The organic extracts were washed with water and saturated sodium chloride solution, dried over anhydrous sodium sulfate, filtered, and concentrated. The residue was purified by flash chromatography employing ethyl acetate as the eluent. The appropriate fractions were combined and concentrated to provide 3.13 g (49%) of 8,13-epoxy-6β-[N-(2-dimethylamino)ethylaminocarbonyloxy]-1α,7β,-9α-trihydroxylabd-14-en-11-one-1,9-dimethylformamide acetal. To a solution of 0.10 g of the 1,9-dimethylformamide acetal, so prepared, in 2 ml of dichloromethane was added 0.022 ml of acetic anhydride. To the solution was added 0.0024 g of 4-dimethylaminopyridine. The reaction mixture was stirred for 2 hrs at room temperature, under nitrogen. An additional 0.021 g of 4-dimethylaminopyridine was added, and the solution was stirred for 24 hrs at room temperature, under nitrogen. The solution was concentrated and purified by flash chromatography, employing 10% methanol/dichloromethane. The appropriate fractions were combined and concentrated to provide product. The hydrochloride salt, prepared by addition of ethereal hydrogen chloride to a solution of the product in ether, had mp 136°–138°.

REACTION SCHEME A

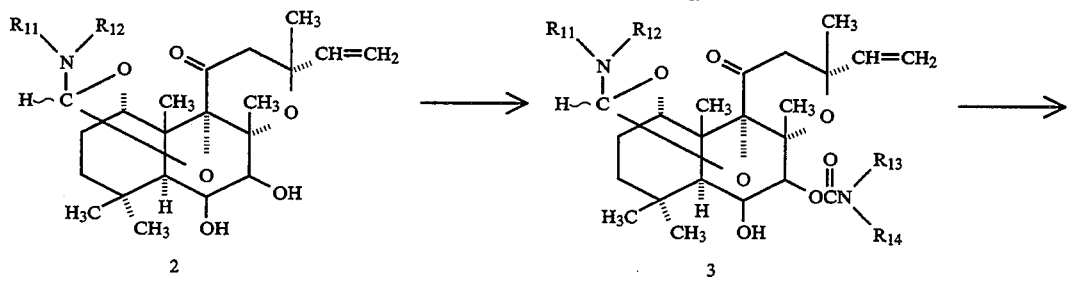

-continued
REACTION SCHEME A
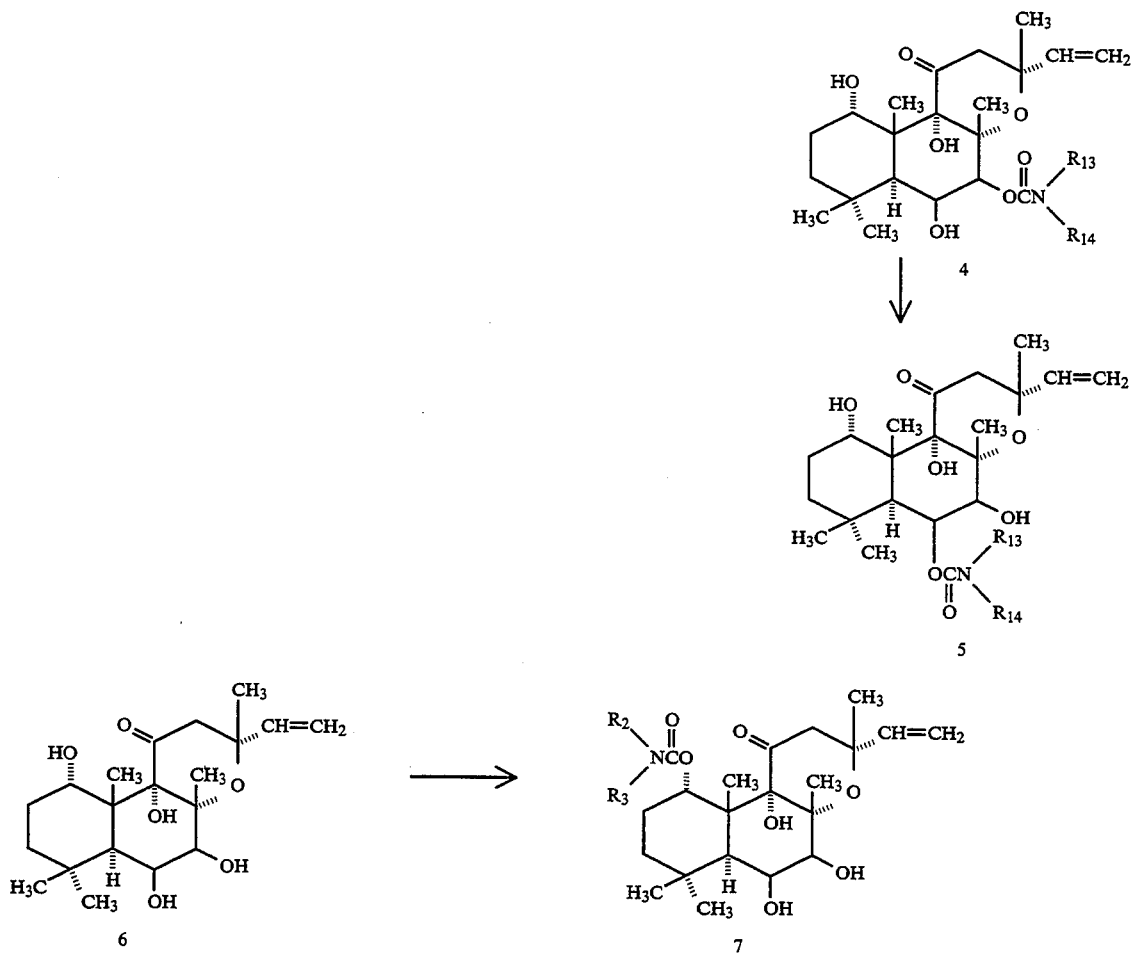
wherein $R_2$, $R_3$, $R_{11}$, $R_{12}$, $R_{13}$, and $R_{14}$ are as hereinbeforedescribed.
REACTION SCHEME B
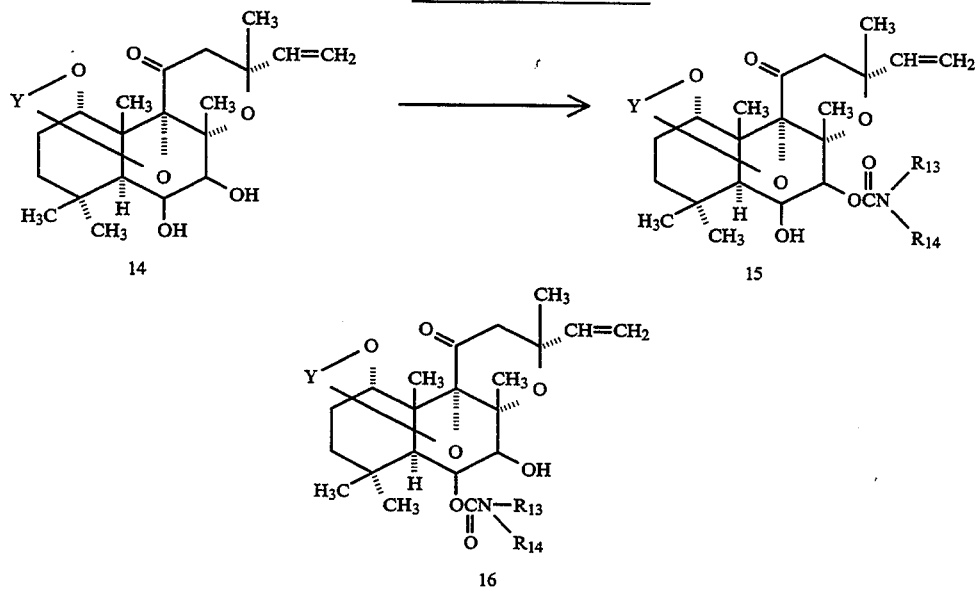
wherein Y, $R_{13}$, and $R_{14}$ are as hereinbeforedescribed.

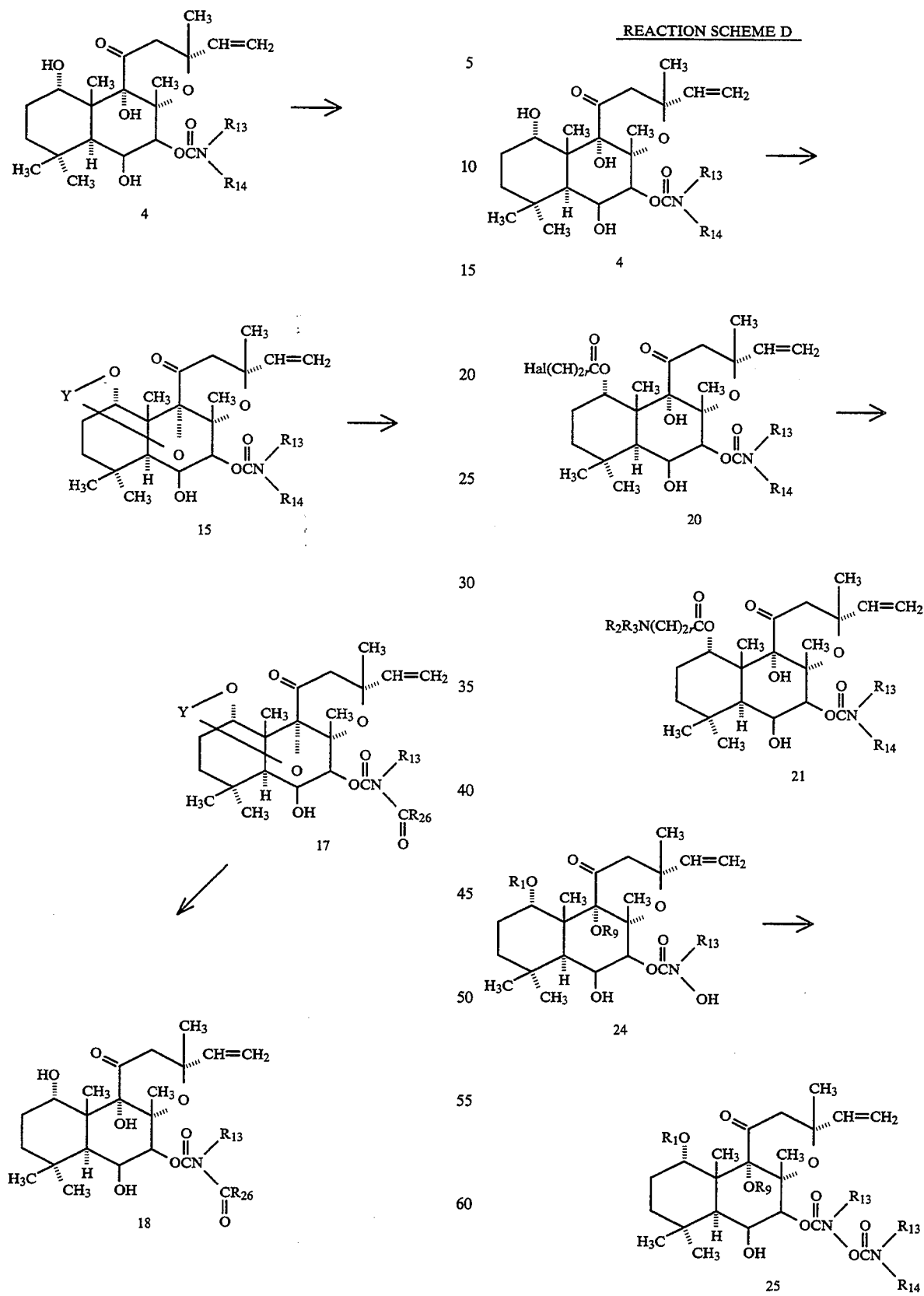
wherein $R_{13}$ and $R_{14}$ are hydrogen, $R_{26}$ is as hereinbeforedescribed and Y is CO.
wherein $R_1$, $R_2$, $R_3$, $R_9$, $R_{13}$, $R_{14}$, r and Hal are as hereinbeforedescribed.

REACTION SCHEME E

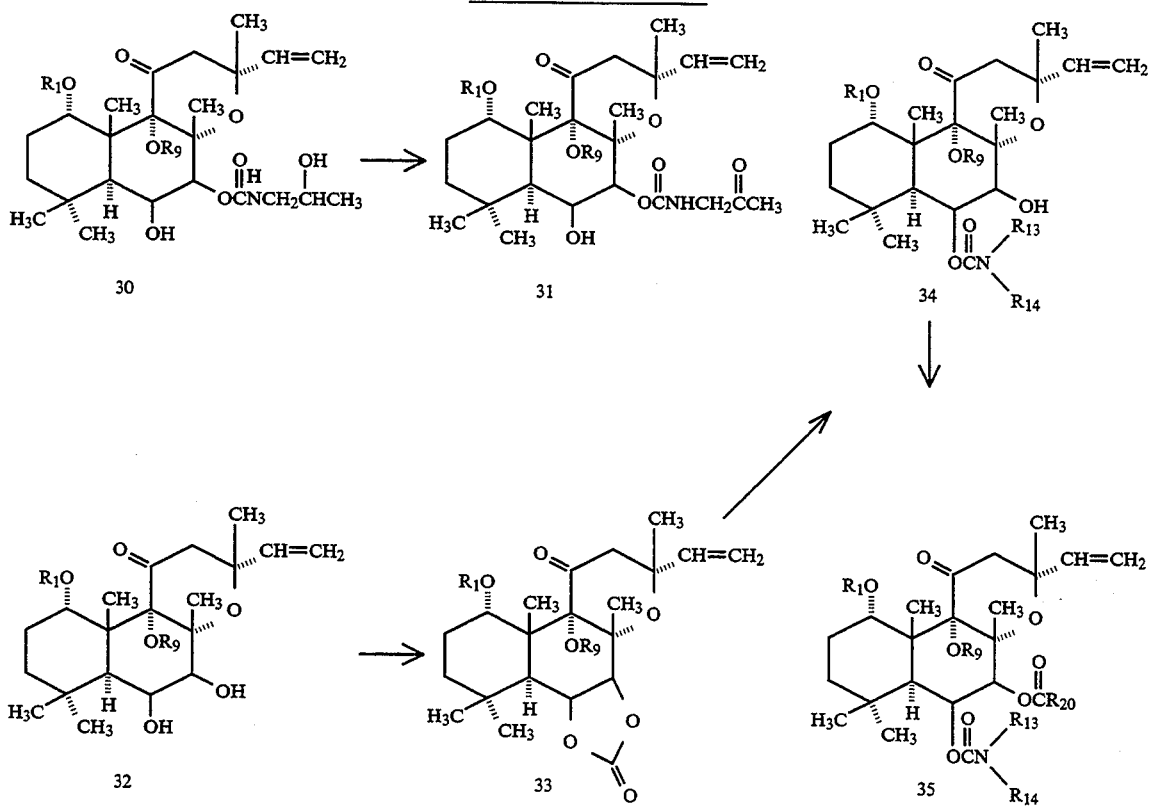

wherein $R_1$ and $R_9$ are hydrogen or taken together from a group $CHNR_{11}R_{12}$ wherein $R_{11}$ and $R_{12}$ are as hereinbeforedescribed and $R_{13}$, $R_{14}$ and $R_{20}$ are as hereinbeforedescribed.

REACTION SCHEME F

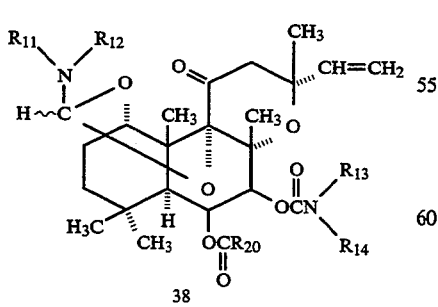

wherein $R_{11}$, $R_{12}$, $R_{13}$, $R_{14}$, and $R_{29}$ are as hereinbeforedescribed.

We claim:
1. A compound of the formula

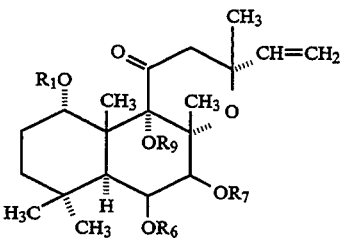

wherein:
(a) $R_1$ and $R_9$ taken together form a group of the formula $-CHNR_{11}R_{12}$ wherein $R_{11}$ and $R_{12}$ are each independently loweralkyl of 1 to 6 carbon atoms; and $R_{11}$ and $R_{12}$ taken together with the nitrogen atom to which they are attached form a group of the formula

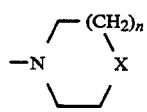

wherein X is O, S, a group of the formula $NR_{19}$ wherein $R_{19}$ is loweralkyl of 1 to 6 carbon atoms or a group of the formula $CHR_4$ wherein $R_4$ is hydrogen, loweralkyl of 1 to 6 carbon atoms or a group of the formula $OR_5$ wherein $R_5$ is hydrogen, loweralkyl of 1 to 6 carbon atoms or a group of the formula

wherein R$_{10}$ is loweralkyl and n is 0 or 1;
(b) R$_6$ and R$_7$ independently are hydrogen, a group of the formula

wherein R$_{20}$ is hydrogen or loweralkyl of 1 to 6 carbon atoms, or a group of the formula

wherein R$_{13}$ is hydrogen, loweralkyl of 2 to 6 carbon atoms, hydroxyloweralkyl of 1 to 6 carbon atoms, loweralkoxyloweralkyl having 1 to 6 carbon atoms in the alkoxy group and 2 to 6 carbon atoms in the alkyl group; or a group of the formula HOCH$_2$CH(OH)CH$_2$—; R$_{14}$ is hydrogen, hydroxyl, loweralkoxy of 1 to 6 carbon atoms, loweralkyl of 1 to 6 carbon atoms, hydroxyloweralkyl of 2 to 6 carbon atoms, loweralkoxyloweralkyl of 1 to 6 carbon atoms in the alkoxy group and 2 to 6 carbon atoms in the alkyl group, loweralkanoyl of 2 to 6 carbon atoms, loweralkanoylloweralkyl of 2 to 6 carbon atoms in the alkanoyl group and 1 to 6 carbon atoms in the alkyl group, a group of the formula

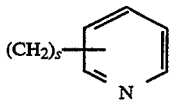

wherein s is 1 or 2, a group of the formula,

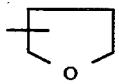

a group of the formula HOCH$_2$CH(OH)CH$_2$—, a group of the formula —(CH$_2$)$_t$NR$_{21}$R$_{22}$ wherein R$_{21}$ and R$_{22}$ are independently loweralkyl of 1 to 6 carbon atoms and t is 0, or 2 to 6, R$_{21}$ and R$_{22}$ taken together with the nitrogen atoms to which they are attached form a group of the formula

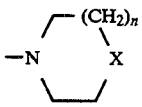

wherein X and n are as above, a group of the formula OR$_{23}$ wherein R$_{23}$ is hydrogen, loweralkyl of 1 to 6 carbon atoms, a group of the formula —(CH$_2$)$_{t'}$NR$_{21}$R$_{22}$ wherein t' is 2 to 6, R$_{21}$ and R$_{22}$ are as above, a group of the formula

wherein R$_{24}$ is hydrogen, loweralkyl of 1 to 6 carbon atoms, lowercycloalkyl of 3 to 6 carbon atoms, loweralkenyl of 2 to 6 carbon atoms, haloloweralkenyl of 2 to 6 carbon atoms, loweralkanoylloweralkyl of 2 to 6 carbon atoms in the alkanoyl group and 1 to 6 carbon atoms in the alkyl group, loweralkoxyloweralkyl of 1 to 6 carbon atoms in each group, loweralkoxycarbonylloweralkyl of 1 to 6 carbon atoms in each group, loweralkylamino of 1 to 6 carbon atoms, lowerdialkylamino of 2 to 6 carbon atoms, a group of the formula

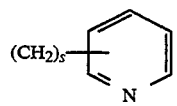

wherein s is as above, a group of the formula

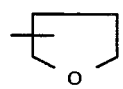

a group of the formula —(CH$_2$)$_{t'}$NR$_{21}$R$_{22}$ wherein R$_{21}$, R$_{22}$ and t' are as above, a group of the formula

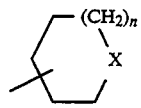

wherein X and n are as above, a group of the formula —(CH$_2$)$_u$N(R$_{25}$)COR$_{26}$, wherein u is 1, 2 or 3 and R$_{25}$ and R$_{26}$ are independently hydrogen or loweralkyl of 1 to 6 carbon atoms, a group of the formula

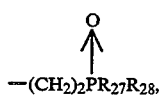

wherein R$_{27}$ and R$_{28}$ are loweralkyl of 1 to 6 carbon atoms, with the proviso that at least one of R$_6$ or R$_7$ is a group of the formula

the optical or geometric isomers thereof; or the pharmaceutically acceptable salts thereof.

2. A compound according to claim 1 wherein R$_1$ and R$_9$ taken together form a group of the formula —CHNR$_{11}$R$_{12}$, wherein R$_{11}$ and R$_{12}$ are as above and R$_6$ or R$_7$ is a group of the formula

wherein $R_{13}$ and $R_{14}$ are as above.

3. A compound according to claim 1 wherein $R_6$ is a group of the formula $$R_{13}R_{14}N\overset{O}{\overset{\|}{C}}-$$

wherein $R_{13}$ and $R_{14}$ are as above and $R_7$ is a group of the formula $$R_{20}\overset{O}{\overset{\|}{C}}-$$

wherein $R_{20}$ is as above.

4. A compound according to claim 1 wherein $R_7$ is a group of the formula $$R_{13}R_{14}N\overset{O}{\overset{\|}{C}}-;$$

wherein $R_{13}$ and $R_{14}$ are as above and $R_6$ is a group of the formula $$R_{20}\overset{O}{\overset{\|}{C}}-$$

wherein $R_{20}$ is as above.

5. The compound according to claim 2 which is 7β-(aminocarbonyloxy)-8,13-epoxy-1α,6β,9α-trihydroxylabd-14-en-11-one-1,9-dimethylformamide acetal.

6. The compound according to claim 2 which is 8,13-epoxy-7β-(N-methylaminocarbonyloxy)-1α,6β,9α-trihydroxylabd-14-en-11-one-1,9-dimethylformamide acetal.

7. The compound according to claim 2 which is 8,13-epoxy-7β-(4-morpholinocarbonyloxy)-1α,6β,9α-trihydroxylabd-14-en-11-one-1,9-dimethylformamide acetal.

8. The compound according to claim 2 which is 8,13-epoxy-7β-(4-hydroxy-1-piperidinocarbonyloxy)-1α,6β,9α-trihydroxylabd-14-en-11-one-1,9-dimethylformamide acetal.

9. The compound according to claim 2 which is 8,13-epoxy-7β-(N-2-hydroxyethylaminocarbonyloxy)-1α,6β, 9α-trihydroxylabd-14-en-11-one-1,9-dimethylformamide acetal.

10. The compound according to claim 2 which is 8,13-epoxy-7β-(2,3-dihydroxypropylaminocarbonyloxy)-1α,6β,9α-trihydroxylabd-14-en-11-one-1,9-dimethylformamide acetal.

11. The compound according to claim 2 which is 8,13-epoxy-7β-(N-hydroxyaminocarbonyloxy)-1α,6β,-9α-trihydroxylabd-14-en-11-one-1,9-dimethylformamide acetal.

12. The compound according to claim 2 which is 8,13-epoxy-7β-(N-methyl-N-hydroxyaminocarbonyloxy)-1α,6β,9α-trihydroxylabd-14-en-11-one-1,9-dimethylformamide acetal.

13. The compound according to claim 2 which is 8,13-epoxy-7β-(N-ethylaminocarbonyloxy)-1α,6β,9α-trihydroxylabd-14-en-11-one-1,9-dimethylformamide acetal.

14. The compound according to claim 2 which is 8,13-epoxy-7β-(N-methoxyaminocarbonyloxy)-1α,6β,-9α-trihydroxylabd-14-en-11-one-1,9-dimethylformamide acetal.

15. The compound according to claim 2 which is 8,13-epoxy-7β-(1-pyrrolidinocarbonyloxy)-1α,6β,9α-trihydroxylabd-14-en-11-one-1,9-dimethylformamide acetal.

16. The compound according to claim 2 which is 7β-(N,N-dimethylaminocarbonyloxy)-8,13-epoxy-1α,6β,9α-trihydroxylabd-14-en-11-one-1,9-dimethylformamide acetal.

17. The compound according to claim 4 which is 7β-(N,N-diethylaminocarbonyloxy)-8,13-epoxy-1α,6β,9α-trihydroxylabd-14-en-11-one-1,9-dimethylformamide acetal.

18. A method of reducing intraocular pressure in mammals comprising administering to a mammal requiring intraocular pressure reduction, an intraocular pressure reducing effective amount of a compound of claim 1.

19. An intraocular pressure reducing composition comprising an inert adjuvant and as the active ingredient, an intraocular pressure reducing effective amount of a compound of claim 1.

20. A compound of the formula wherein $R_{11}$ and $R_{12}$ are each independently loweralkyl of 1 to 6 carbon atoms; and $R_{11}$ and $R_{12}$ taken together with the nitrogen atom to which they are attached form a group of the formula wherein X is O, S, a group of the formula $NR_{19}$ wherein $R_{19}$ is loweralkyl of 1 to 6 carbon atoms or a group of the formula $CHR_4$ wherein $R_4$ is hydrogen, loweralkyl of 1 to 6 carbon atoms or a group of the formula $OR_5$ wherein $R_5$ is hydrogen, loweralkyl of 1 to 6 carbon atoms or a group of the formula $$\overset{O}{\overset{\|}{C}}R_{10}$$

wherein $R_{10}$ is loweralkyl of 1 to 6 carbon atoms and n is 0 or 1.

21. A compound according to claim 2 which is 8,13-epoxy-7β-[N,N-bis-2-hydroxyethylaminocarbonyloxy)-1α,6β,9α-trihydroxylabd-14-en-11-one- 1,9-dimethylformamide acetal.

22. A compound according to claim 2 which is 8,13-epoxy-7β-(N-propylaminocarbonyloxy)-1α,6β,9α-trihydroxylabd-14-en-11-one-1,9-dimethylformamide acetal.

23. A compound according to claim 2 which is 8,13-epoxy-7β-(N-ethoxyaminocarbonyloxy)-1α,6β,9α- trihydroxylabd-14-en-11-one-1,9-dimethylformamide acetal.

24. A compound according to claim 2 which is 8,13-epoxy-6β-[N-(2hyroxyethyl)aminocarbonyloxy]-1α,7β,9α-trihydroxylabd-14-en-11-one-1,9-dimethylformamide acetal.

25. A compound according to claim 2 which is 8,13-epoxy-6β-(1-pyrrolidinocarbonyloxy)-1α,7β,9α-trihydroxylabd-14-en-11-one-1,9-dimethylformamide acetal.

26. A compound according to claim 2 which is 8,13-epoxy-7β-(N-methyl-N-propionylaminocarbonyloxy)-1α,6β,9α-trihydroxylabd-14-en-11-one-1,9-dimethylformamide acetal.

27. A compound according to claim 2 which is 8,13-epoxy-7β-[N-(3-hydroxypropyl)aminocarbonyloxy]-1α,6β,9α-labd-14-en-11-one-1,9-dimethylformamide acetal.

28. A compound according to claim 2 which is 8,13-epoxy-7β-[N-(2-oxopropyl)aminocarbonyloxy]-1α,6β,9α-trihydroxylabd-14-en-11-one-1,9-dimethylformamide acetal.

29. A compound according to claim 2 which is 7β-[N-(2-dimethylaminoethyl)aminocarbonyloxy]-8,13-epoxy]-1α,6β,9α-trihydroxylabd-14-en-11-one-1,9-dimethylformamide acetal.

30. A compound according to claim 2 which is 8,13-epoxy-7β-[N-(2-piperidinoethyl)aminocarbonyloxy]-1α,6β,9α-trihydroxylabd-14-en-11-one-1,9-dimethylformamide acetal.

31. A compound according to claim 2 which is 8,13-epoxy-7β-[1-(4-methylpiperazin-1-yl)carbonyloxy]-1α,6β,9α-trihydroxylabd-14-en-11-one-1,9-dimethylformamide acetal.

32. A compound according to claim 2 which is 8,13-epoxy-7β-[N-2-(pyridin-2-ylethyl)aminocarbonyloxy]-1α,6β,9α-trihydroxylabd-14-en-11-one-1,9-dimethylformamide acetal.

33. A compound according to claim 2 which is 7β-[N-(3-(dimethylaminopropyl)aminocarbonyloxy]-1α,6β,9α-trihydroxylabd-14-en-11-one-1,9-dimethylformamide acetal.

34. A compound according to claim 2 which is 8,13-epoxy-7β-[N-2-(pyridylmethyl)aminocarbonyloxy]-1α,7β,9α-trihydroxylabd-14-en-11-one-1,9-dimethylformamide acetal.

35. A compound according to claim 2 which is 6β-[N-(3-dimethylaminopropyl)aminocarbonyloxy]-1α,7β,9α-trihydroxylabd-14-en-11-one-1,9-dimethylformamide acetal.

36. A compound according to claim 2 which is 8,13-epoxy-6β-(4-methylpiperazinyl)carbonyloxy-1α,7β,9α-trihydroxylabd-14-en-11-one-1,9-dimethylformamide acetal.

37. A compound according to claim 2 which is 8,13-epoxy-6β-(4-pyridylmethyl)aminocarbonyloxy-1α,7β,9α-trihydroxylabd-14-en-11-one-1,9-dimethylformamide acetal.

38. A compound according to claim 2 which is 8,13-epoxy-6β-[N-2-(pyridylmethyl)aminocarbonyloxy]-1α,7β,9α-trihydroxylabd-14-en-11-one-1,9-dimethylformamide acetal.

39. The compound which is 8,13-epoxy-6β,7β-bis(1-imidazolidylcarbonyloxy)-1α,9α-dihydroxylabd-14-en-11-one-1,9-dimethylformamide acetal.

40. The compound which is 8,13-epoxy-1α,6β,7β,9α-tetrahydroxylabd-14-en-11-one-6β,7β-carbonate-1,9-dimethylformamide acetal.

41. A compound according to claim 2 which is 8,13-epoxy-7β-[N,N-bis(2-hydroxyethyl)aminocarbonyloxy-1α,6β,9α-trihydroxylabd-14-en-11-one-1,9-dimethyl formamide acetal.

42. A compound according to claim 1 which is 7β-acetoxy-1α,9α-dihydroxy-6β-[N-(2-dimethylaminoethyl)aminocarbonyloxy]-8,13-epoxylabd-14-en-11-one 1,9-dimethylformamide acetal.

43. A compound according to claim 1 which is 6β-[N-(2-dimethylaminoethyl)aminocarbonyloxy]-8,13-epoxy-1α,7β,9α-trihydroxylabd-14-en-11-one-1,9-dimethylformamide acetal.

44. A compound according to claim 2 wherein $R_{13}$ hydrogen and $R_{14}$ is a group of the formula

wherein $R_{24}$ is loweralkyl of 1 to 6 carbon atoms or a group of the formula

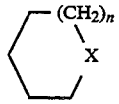

wherein n and X are as above.

* * * * *